United States Patent [19]

DesMarais et al.

[11] Patent Number: 5,331,015

[45] Date of Patent: Jul. 19, 1994

[54] ABSORBENT FOAM MATERIALS FOR AQUEOUS BODY FLUIDS AND ABSORBENT ARTICLES CONTAINING SUCH MATERIALS

[75] Inventors: Thomas A. DesMarais, Norwood; Keith J. Stone; Hugh A. Thompson, both of Fairfield; Gerald A. Young, Cincinnati; Gary D. LaVon, Harrison; John C. Dyer, Cincinnati, all of Ohio

[73] Assignee: The Procter & Gamble Company, Cincinnati, Ohio

[21] Appl. No.: 156,858

[22] Filed: Nov. 23, 1993

Related U.S. Application Data

[63] Continuation of Ser. No. 42,363, Apr. 2, 1993, Pat. No. 5,268,224.

[51] Int. Cl.$^5$ .......................... C08J 9/28; B32B 3/26; A61F 13/15
[52] U.S. Cl. ........................................ 521/62; 428/286; 428/298; 428/314.2; 428/315.5; 428/319.3; 428/319.9; 521/63; 521/64; 521/149; 521/150; 604/369
[58] Field of Search .............. 521/62, 63, 64, 149, 521/150; 428/286, 298, 314.2, 315.5, 319.3, 319.9; 604/369

[56] References Cited

U.S. PATENT DOCUMENTS

| | | | |
|---|---|---|---|
| 3,255,127 | 6/1966 | von Bonin | 260/2.5 |
| 3,431,911 | 3/1969 | Meisel | 128/287 |
| 3,563,243 | 2/1971 | Lindquist | 128/287 |
| 3,673,142 | 6/1972 | Saunders et al. | 524/458 |

(List continued on next page.)

FOREIGN PATENT DOCUMENTS

| | | | |
|---|---|---|---|
| 2017570 | 11/1990 | Canada | B01J 20/22 |
| 299122 | 1/1989 | European Pat. Off. | C08J 9/02 |
| 299762 | 1/1989 | European Pat. Off. | C08F 2/32 |
| 2-239863 | 9/1990 | Japan | |
| 2-289608 | 11/1990 | Japan | |
| 3-49759 | 3/1991 | Japan | A61F 13/15 |
| 1493356 | 11/1977 | United Kingdom | |

OTHER PUBLICATIONS

Lissant et al, "Structure of High–Internal–Phase–Ratio Emulsions", Journal of Colloid and Interface Science, vol. 47, No. 2, May, 1974.

Lissant et al, "A Study of Medium and High Internal Phase Ratio Water/Polymer Emulsions", Journal of Colloid and Interface Science, vol. 42, No. 1, Jan. 1973.

Lissant, "The Geometry of High–Internal Phase–Ratio Emulsions", Journal of Colloid and Interface Science, vol. 22, 462–468 (1966).

Aubert et al, "Low–Density, Microcellular Polystyrene Foams", Polymer, 1985, vol. 26, Dec.

Weber et al, "New Melamine–Based Elastic Foam", Kunststoffe 75 (1985) 11, pp. 843–848.

English translation of p. 733 of the Oct. 1, 1988 edition of Chemical Products published by Japan Chemical Industrial Daily News.

*Primary Examiner*—Morton Foelak
*Attorney, Agent, or Firm*—Eric W. Guttag; E. Kelly Linman

[57] ABSTRACT

Disclosed are absorbent foam materials suitable for use as or in the absorbent cores of absorbent articles, such as diapers which absorb and retain aqueous body fluids. Such foam materials comprise hydrophilic, flexible open-celled structures which are preferably prepared by polymerizing high internal phase (HIPE) water-in-oil emulsions. Such foam materials have a pore volume of from about 12 to 100 mL/g, and a capillary suction specific surface area of from about 0.5 to 5.0 m$^2$/g. These materials also exhibit a resistance to compression deflection such that a confining pressure of 5.1 kPa produces after 15 minutes a strain of from about 5% to 95% compression when the material is saturated at 37° C. to its free absorbent capacity with synthetic urine.

11 Claims, 3 Drawing Sheets

U.S. PATENT DOCUMENTS

| | | | |
|---|---|---|---|
| 3,734,867 | 5/1973 | Will | 260/2.5 R |
| 3,763,056 | 10/1973 | Will | 260/2.5 L |
| 4,029,100 | 6/1977 | Karami | 128/284 |
| 4,394,930 | 7/1983 | Korpman | 220/444 |
| 4,473,611 | 9/1984 | Haq | 428/198 |
| 4,522,953 | 6/1985 | Barby et al. | 521/64 |
| 4,554,297 | 11/1985 | Dabi | 521/178 |
| 4,603,069 | 7/1986 | Haq et al. | 428/76 |
| 4,606,958 | 8/1986 | Haq et al. | 428/68 |
| 4,611,014 | 9/1986 | Jones et al. | 521/146 |
| 4,612,334 | 9/1986 | Jones et al. | 521/146 |
| 4,659,564 | 4/1987 | Cox et al. | 424/65 |
| 4,668,709 | 5/1987 | Jones et al. | 521/146 |
| 4,788,225 | 11/1988 | Edwards et al. | 521/147 |
| 4,797,310 | 1/1989 | Barby et al. | 428/71 |
| 4,839,395 | 6/1989 | Masamizu et al. | 521/56 |
| 4,957,810 | 9/1990 | Eleouet et al. | 428/306.6 |
| 4,985,467 | 1/1991 | Kelly et al. | 521/52 |
| 5,147,345 | 9/1992 | Young et al. | 604/378 |
| 5,149,720 | 9/1992 | DesMarais et al. | 521/63 |
| 5,198,472 | 3/1993 | DesMarais et al. | 521/63 |
| 5,250,576 | 10/1993 | DesMarais et al. | 521/63 |
| 5,260,345 | 11/1993 | DesMarais et al. | |
| 5,268,224 | 12/1993 | DesMarais | 521/149 |

0 10u

ABSORBENT FOAM MATERIALS FOR AQUEOUS BODY FLUIDS AND ABSORBENT ARTICLES CONTAINING SUCH MATERIALS

This is a continuation of application Ser. No. 08/042,363, filed on Apr. 2, 1993, now U.S. Pat. No. 5,268,224.

FIELD OF THE INVENTION

The present invention relates to flexible, microporous, open-celled polymeric foam materials having fluid absorption and retention characteristics which make such materials particularly suitable for use in body fluid, e.g., urine, absorbing articles such as diapers, adult incontinence garments, bed pads, panty liners, sweatbands, shoe liners and the like.

BACKGROUND OF THE INVENTION

The development of highly absorbent materials and structures for use in diapers, catamenial products, bandages, and the like, is the subject of substantial commercial interest. Originally, such products relied on various cloth or cotton fibers to provide absorbency. Further progress in the field of absorbent materials and structures came with the development of various air-laid cellulosic pulp batts which, in general, will absorb up to 5-6 times their own weight of aqueous body fluids such as urine. Most recently, the use of absorbent gelling materials, such as the polyacrylates, in combination with cellulosic fibers has substantially increased the absorbent capacity of absorbent articles such as diapers and has allowed the manufacture of the relatively thin diapers which are currently commercially marketed. However, even with these improvements, the search for still better absorbent materials and structures continues.

To the uninitiated, it might seem reasonable to suggest that ordinary sponge materials which, in their broadest aspects, might be considered to be open-celled foams, would be quite useful in absorbent structures and articles. For example, both natural sponges and artificial cellulosic sponges have been used to mop up water and other fluids since time immemorial. However, on closer consideration, it will be appreciated that such sponges are not particularly suitable in high performance body fluid absorbing articles of the type currently envisioned. For example, absorbent articles are, initially, used in the dry state. It is well known that many dry sponge materials are quite stiff (rigid) and harsh feeling to the skin and, therefore, would not be suitable for use in diapers and other incontinence products. Furthermore many common sponge materials can have non-uniform cell sizes and partially or completely closed cells which hinder fluid wicking through and fluid retention by the sponge. Finally, while common sponge materials can imbibe substantial quantities of aqueous fluids, they can also release the imbibed fluids with very little pressure. Accordingly, such sponge materials would be entirely unsuitable for use in situations where the absorbent structure is used under conditions wherein pressure is applied, for example, when a diapered child sits down.

Besides common "sponges," the literature and commercial practice are replete with descriptions of various types of polymeric foams which can imbibe a variety of fluids for a variety of purposes. It is also known to employ certain types of polymeric foam materials as elements of absorbent articles such as diapers and catamenial products. For example, Karami; U.S. Pat. No. 4,029,100, Issued Jun. 14, 1977 discloses a shape-retaining diaper which can employ a foam element in the crotch area of its absorbent pad assembly in order to provide high wet resiliency for the pad assembly.

Certain types of foam materials have also been disclosed as being useful in absorbent articles for the purpose of actually imbibing, wicking and/or retaining aqueous body fluids. For example, Lindquist; U.S. Pat. No. 3,563,243; Issued Feb. 16, 1971 discloses an absorbent pad for diapers and the like wherein the primary absorbent therein is a hydrophilic foam sheet formed from hydrophilic polymers. Such foam sheets are said to be formed by combining poly(oxyethylene) glycols with diisocyanates. Dabi; U.S. Pat. No. 4,554,297; Issued Nov. 19, 1985 discloses body fluid absorbing cellular polymers which can be used in diapers or catamenial products. Such cellular polymers comprise the reaction products of at least one epoxy resin and an amine-terminated poly(alkylene oxide). Garvey et al; U.S. Pat. No. 4,740,528; Issued Apr. 26, 1988 discloses absorbent composite structures such as diapers, feminine care products and the like, which contain a sponge absorbent composition made from a certain type of super-wicking, crosslinked polyurethane foam.

Notwithstanding the known uses of various polymeric foam types as elements in absorbent articles for body fluids, there is a continuing need to identify additional absorbent foam materials having an optimized combination of features and characteristics which render such foams especially useful in commercially marketed absorbent products such as diapers. It has now been determined that optimized absorbent foams for body fluids, and especially foams intended for use in diapers and adult incontinence products, should have the following characteristics:

a) Flexibility and preferably recovery from compression, for comfort and performance;
b) Acceptable fluid acquisition rate, in order for the foam to rapidly accept and imbibe gushes of urine or other fluids;
c) Relatively good wicking and fluid distribution characteristics in order for the foam to transport the imbibed urine or other fluid away from the zone wherein the fluid initially impinges onto the foam and into the unused balance of the foam structure, thereby allowing for subsequent gushes of fluid to be accommodated;
d) Relatively high total storage capacity with relatively high fluid capacity under load, i.e., under compressive pressure; and
e) Relatively low density in order for the foam to exhibit suitably high total storage capacity and to comprise a thin soft material.
f) Relatively greater affinity for absorbing body fluids than exhibited by other absorbent article components so that the foam material can drain (partition) fluids from these other components and keep such fluid stored within the foam structure.

It will be appreciated that absorbent foams having the foregoing characteristics would provide the features of fluid acquisition, transport, storage which are required for use in high performance absorbent articles. Optimized foams would, preferably, also be soft to the touch. Of course, absorbent foams intended for use in contact with or in proximity to the skin should cause no damage or irritation to the skin nor expose the user to toxic chemicals. Since they are intended for use in disposable articles such as diapers, such preferred optimized foams should also be relatively inexpensive and easy to manufacture and should be compatible with responsible solid waste disposal systems such as those based on landfills, incineration and/or composting.

It will also be appreciated by the manufacturer of absorbent articles that optimized absorbent foam materials of the type hereinbefore described would represent a substantial advance in the industry. Absorbent articles containing such foams would possess desirable wet integrity, would enable suitable fit through the entire period the article was being worn, would not degrade in shape during use, and would provide desirable skin dryness.

Absorbent articles containing such foam structures would also be easier to manufacture on a commercial scale. For example, diaper product cores could be simply stamped out of continuous foam sheets and could be designed to have considerably greater integrity and uniformity than air-laid absorbent cores. Such foams could furthermore be molded in any desired shape, or even formed into integral, unitary diapers or panty-like structures. Alternatively, such foam materials could be combined, e.g., blended, with other conventional absorbent structure components.

The present invention identifies the parameters which define optimized absorbent foam materials that are especially adapted for use in absorbent articles for body fluids such as urine. The invention herein also provides absorbent foams which overcome a number of the drawbacks of foam materials heretofore used in body fluid absorbing articles.

SUMMARY OF THE INVENTION

In its composition aspects, the present invention relates to a certain type of polymeric foam material which is especially suitable for absorbing and retaining aqueous body fluids, e.g. urine. Such a foam material comprises a hydrophilic, flexible structure formed from a plurality of interconnected open cells. This cellular foam structure has, in use as an absorbent material, a pore volume of from about 12 to 100 mL/g and a specific surface area of from about 0.5 to 5.0 m$^2$/g as determined by capillary suction. The foam structure also will exhibit a resistance to compression deflection such that a confining pressure of 5.1 kPa produces, after 15 minutes, a strain of from about 5% to 95% compression of the structure when it is saturated to its free absorbent capacity with 65±5 dyne/cm synthetic urine at 37° C.

Preferred absorbent foam materials having these characteristics can be prepared by polymerizing a specific type of water-in-oil emulsion having a relatively smaller amount of an oil phase and a relatively greater amount of a water phase. This type of polymerizable emulsion in general is known in the art as a high internal phase emulsion or "HIPE".

The oil phase forming the particular water-in-oil HIPE emulsions which can be used to prepare the preferred absorbent foams herein comprises from about 3% to 41% by weight of a substantially water-insoluble, monofunctional glassy monomer component, from about 27% to 73% by weight of a substantially water-insoluble, monofunctional rubbery comonomer component; from about 8% to 30% by weight of a substantially water-insoluble polyfunctional cross-linking agent component and from about 2% to 33% by weight of an emulsifier component which is soluble in the oil phase and which will enable realization of a stable emulsion for polymerization. The water or "internal" phase forming the water-in-oil HIPE emulsions which can be used to prepare such preferred foams comprises an aqueous solution containing from about 0.2% to 40% by weight of a water-soluble electrolyte. The weight ratio of the water phase to the oil phase in these water-in-oil HIPE emulsions ranges from about 12:1 to 100:1.

The water-in-oil emulsions which can be used to prepare the preferred absorbent foam material of this invention are polymerized under conditions that provide open-celled foam structures having the structural and resistance to compression deflection characteristics as hereinbefore set forth. Subsequent post-polymerization treatment of such foams will frequently be necessary to render the foam materials suitably hydrophilic and ready for absorbing aqueous body fluids.

In its article aspects, the present invention relates to absorbent articles for incontinence management such as diapers which utilize the polymeric foam absorbent materials herein as at least a portion of their fluid-absorbing "core" element. Thus, in the broadest sense, the absorbent articles of the present invention will generally comprise a relatively liquid-impervious backing sheet (or water impervious "skin" on the foam itself) and a polymeric foam absorbent material of the type hereinbefore described. The absorbent polymeric foam material is associated with the backing sheet in such a manner that the foam absorbent material is situated between the backing sheet and the fluid discharge region of the wearer of the absorbent article.

DETAILED DESCRIPTION OF THE INVENTION

Figure 1:
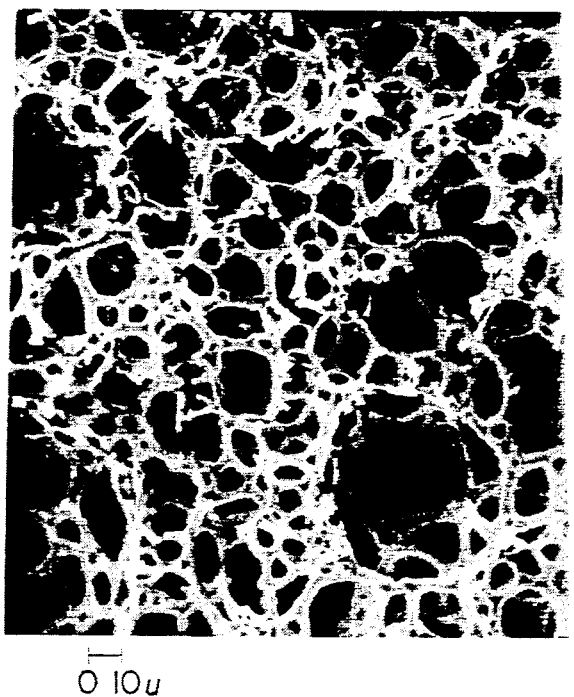
FIG. 1 of the drawings is a photomicrograph of the interstices of a typical absorbent HIPE foam of the present invention.

As noted, the present invention is based on the use of a certain type of very specifically defined polymeric foam material as an absorbent for discharged aqueous body fluids such as urine. These polymeric foam absorbents can thus be employed as, or as part of, the absorbent cores of absorbent articles such as diapers, incontinence briefs or pads, training pants, and the like.

Polymeric foams can in general be characterized as the structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized dispersion can be in the form of a porous solidified structure which is an aggregate of cells, the boundaries or walls of which cells comprise solid polymerized material. The cells themselves contain the relatively monomer-free gas or relatively monomer-free liquid which, prior to polymerization, had formed the "bubbles" in the liquid dispersion.

As described more fully hereafter, the preferred polymeric foam materials useful as absorbents in the present invention are those prepared by polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms the dispersed "bubbles" surrounded by the continuous polymerizable monomer-containing oil phase. Subsequent polymerization of the monomers in the continuous oil phase forms the cellular foam structure. The aqueous liquid remaining in the foam structure formed upon polymerization can be removed by pressing and/or drying the foam.

Polymeric foams, including the preferred foams prepared from the water-in-oil emulsions herein, may be relatively closed-celled or relatively open-celled in character, depending upon whether and/or the extent to which, the cell walls or boundaries, i.e., the cell windows, are filled or taken up with polymeric material. The polymeric foam materials useful in the absorbent articles and structures of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other with i n the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 1. For purposes of the present invention, a foam material is "open-celled" if at least 80% of the cells in the foam structure are in fluid communication with at least one adjacent cell. Alternatively, a foam material can be considered to be substantially open-celled if it has an available pore volume, as described hereinafter, which exceeds the minimum value for this parameter also as set forth hereinafter.

In addition to being open-celled, the polymeric foam absorbents of this invention are hydrophilic in character. The foams herein must be sufficiently hydrophilic to permit the foam to absorb aqueous body fluids in the amounts hereinafter specified. As discussed hereinafter with respect to preferred foam types and methods of foam preparation, the internal surfaces of the foams herein may be rendered hydrophilic by virtue of the particular monomers selected for use in preparing the polymeric foams, by virtue of residual hydrophilizing agents left in the foam structure after polymerization or by virtue of selected post-polymerization foam treatment procedures which can be used to alter the surface energy of the material which forms the foam structure.

The extent to which polymeric foam structures such as those of this invention are "hydrophilic" can be quantified by referencing the "adhesion tension" exhibited by such foams in contact with an absorbable test liquid. Adhesion tension is defined by the formula $$AT = \gamma \cos \theta$$

wherein
AT is adhesion tension in dynes/cm;
$\gamma$ is the surface tension of a test liquid absorbed by the foam material in dynes/cm;
$\theta$ is the contact angle in degrees between the surface of foam polymer material and the vector which is tangent to the test liquid at the point that the test liquid contacts the foam polymer surface.

For any given hydrophilic foam material, the adhesion tension exhibited by the foam can be determined experimentally using a procedure whereby weight uptake of a test liquid, e.g., synthetic urine, is measured for a foam sample of known dimensions and capillary suction specific surface area. Such a procedure is described in greater detail in the TEST METHODS section hereinafter. The foams which are useful as absorbents in the present invention are generally those which have been rendered hydrophilic to the extent that they exhibit an adhesion tension of from about 15 to 65 dynes/cm, more preferably from about 20 to 65 dynes/cm, as determined by capillary suction uptake of synthetic urine having a surface tension of 65±5 dynes/cm.

In addition to being "open-celled" and "hydrophilic", the polymeric foam materials useful in the present invention are those having a specific set of structural and mechanical properties, features or characteristics. It has been discovered that polymeric foams having such selected structural and mechanical properties, features and/or characteristics will as a consequence thereof also possess performance, e.g., fluid handling, properties which render such foams especially suitable and useful as absorbents for aqueous body fluids.

I) STRUCTURAL FEATURES

Specific somewhat interrelated and interdependent structural properties have been identified as being essential to the realization of foam absorbents which are especially suitable for absorbing aqueous body fluids. It should be understood that the foam materials of the present invention may have structural properties which are different from those specified hereinafter at some point prior to contact between the foam and the aqueous body fluid to be absorbed. For example, during their manufacture, shipping, storage, etc., the foams herein may have pore volume, specific surface area, density and/or cell size values outside of the ranges set forth hereinafter for these parameters. However, such foam absorbent structures are nevertheless still within the scope of this invention if they later undergo physical or rheological changes so that they then have the requisite values specified hereinafter for these structural properties at least at some point during the period of subsequent contact between the absorbent structure and the aqueous body fluid to be absorbed thereby. Such essential and preferred structural properties of the foam absorbents herein can be summarized as follows:

A) Pore Volume

Pore volume is a measure of the volume of the openings or cells in a porous foam structure per unit mass of solid material (polymer structure plus any residual solids) which forms the foam structure. Pore volume can be important in influencing a number of performance and mechanical features of the absorbent foams herein. Such performance and mechanical features include absorbent capacity of the foams for aqueous body fluids, the extent and rate of fluid distribution within the structure by wicking of absorbed aqueous fluids from one part of the absorbent foam to another, foam flexibility and foam compression deflection characteristics.

Pore volume may be determined by any suitable experimental method which will give an accurate indication of the actual pore volume of the structure. Such experimental methods will generally involve the measurement of the volume and/or mass of a test liquid which can be introduced into the foam structure and which therefore is representative of the volume occupied by the open cells of the foam. For this reason the pore volume parameter of the foams herein may also be referred to as "available pore volume."

One conventional way for determining available pore volume experimentally involves the introduction of a low surface tension liquid such as isopropanol into the foam structure from outside the foam structure. A procedure for determining available pore volume using isopropanol is set forth hereinafter in the TEST METHODS section. It should be understood, however, that alternative test liquids and procedures may also be used to determine available pore volume.

The pore volume of the absorbent foams useful herein can be influenced and controlled by adjusting a number of foam composition and processing features. For example, with the preferred HIPE emulsion-based foams herein, these pore volume influencing features can include the water-to-oil ratio of the HIPE emulsion, type and amount of water phase electrolyte used, type and amount of oil phase emulsifier used, post-polymerization foam compression steps to effect washing and/or densification of the foam and degree of recovery of the polymerized foam structure after such compression steps.

The foam materials of the present invention will generally have a pore volume of from about 12 to 100 mL/g; more preferably from about 20 to 70 mL/g and most preferably from about 25 to 50 mL/g. Such ranges for pore volume are intended to be an "inclusive" definition of theoretical pore volume for the foams encompassed by this invention. Thus if any experimental method which can reasonably be expected to give measurements approximating theoretical pore volume provides values within the foregoing ranges, then the foam materials tested by any such method are within the scope of this invention.

B) Capillary Suction Specific Surface Area

Another essential structural feature of the foam materials herein is a certain capillary suction specific surface area. Capillary suction specific surface area is, in general, a measure of the test-liquid-accessible surface area of the polymeric network forming a particular foam per unit mass of the bulk foam material (polymer structural material plus solid residual material). Capillary suction specific surface area is determined both by the dimensions (i.e., diameter) of the cellular units in the foam and by the size (length, width and thickness) of the struts which form such cellular units. Capillary suction specific surface area is thus a way of quantifying the total amount of solid surface provided by the foam network to the extent that such a surface participates in absorbency.

The capillary suction specific surface area of an open-celled foam structure such as the absorbent foams herein is the feature of the foam that influences the capillarity (or capillary suction) exhibited by the foam. It has been found that foam capillarity must be controlled and selected so that the foam materials herein have sufficient capillarity to provide acceptable fluid retention while still allowing some wicking of the fluid to occur within the foam structure. Adjustment of capillary suction specific surface area, as well as control of the hydrophilicity of the foam polymer surfaces, is thus the means for providing the requisite degree of capillarity for the absorbent foams of this invention. Foams of relatively high capillary suction specific surface area provide the very desirable combination of high capacity (and low density) and high capillarity. High specific surface area is a consequence of the fineness of the struts making up the foam structure.

The capillary suction specific surface area of the foam absorbents herein is influenced and controlled by adjusting many of the same composition and processing parameters which affect the foam pore volume. For HIPE emulsion-based foams, composition parameters include the water-to-oil ratio of the HIPE emulsion, and the type and amounts of monomers, emulsifiers, and electrolytes utilized in the HIPE emulsion. Process parameters affecting capillary suction specific surface area include mixing energy and temperature.

As noted, for purposes of this invention, the specific surface area of any given foam material being contemplated for use as or in the present invention can and will usually be determined by a procedure which involves the principle of capillary suction. In such a procedure, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section hereinafter. Any reasonable alternative method for determining capillary suction specific surface area may also be utilized.

The open-celled, porous absorbent foams which are useful in the present invention are those which are prepared to have certain capillary suction specific surface area characteristics. In particular, the foams herein will have a capillary suction specific surface area ranging from about 0.5 to 5.0 $m^2/g$, more preferably from about 0.75 to 4.5 $m^2/g$, most preferably from about 1.0 to 4.0 $m^2/g$. It has been discovered that hydrophilic foams having such capillary suction specific surface area values will generally possess an especially desirable balance of absorbent capacity, fluid-retaining and fluid-wicking or distribution characteristics for aqueous body liquids such as urine.

C) Supplemental or Alternative Structural Features

Two additional structural features of the absorbent foams herein which are interrelated with pore volume and capillary suction specific surface area and which can be used as supplemental or alternative ways of characterizing the foams of this invention are foam density and the average size or diameter of the cells making up the foam. Each of these two supplemental/alternative structural features is described as follows:

1) Foam Density

Density of the foam materials herein, like pore volume and capillary suction specific surface area, can influence a number of performance and mechanical characteristics of the absorbent foams herein. These include absorbent capacity for aqueous body fluids, extent and rate of fluid distribution within the foam and foam flexibility and compression deflection characteristics. Importantly also, the density of the foam absorbent structures herein can determine the cost effectiveness of such structures.

Foam density in grams of foam per cubic centimeter of foam volume in air is specified here in on a dry basis. Thus the amount of absorbed aqueous liquid, e.g., that residual liquid which may be left in the foam, for example, after HIPE emulsion polymerization, washing and/or hydrophilization, is disregarded in calculating and expressing foam density. Foam density as specified herein does include, however, residual sol id material such as electrolyte, emulsifiers, hydrophilizing agents, etc., in the polymerized foam. Such residual material may, in fact, contribute significant mass to the foam material.

Any suitable gravimetric procedure which will provide a determination of mass of solid foam material per unit volume of foam structure can be used to measure foam density. For example, an ASTM gravimetric procedure described more fully in the TEST METHODS section hereinafter is one method which may be employed for density determination. For those situations where the foam sample preparation procedures (drying, aging, preflexing, etc.,) might inadvertently alter the density measurements obtained, then alternate density determination tests may also be utilized. Such alternative methods, for example, might include gravimetric density measurements using a test liquid absorbed within the foam material. This type of density determination method can be useful for characterizing very low density foams such as the foams herein wherein the dry density approximates the inverse of the pore volume of the foam. [See Chatterjee, "Absorbency," *Textile Science and Technology*, Vol. 7, 1985, p. 41.] As with pore volume and capillary suction specific surface area, the ranges for foam density set forth hereinafter are intended to be inclusive, i.e., they are intended to encompass density values that may be determined by any reasonable experimental test method.

The foam absorbents of the present invention will preferably have dry basis density values which range from about 0.01 to 0.08 g/cm$^3$, more preferably from about 0.014 to about 0.05 g/cm$^3$, and most preferably from about 0.02 to 0.04 g/cm$^3$, at the time such foam absorbents encounter aqueous fluids to be absorbed. Density of foam materials can be adjusted to within the foregoing ranges by controlling many of the same foam composition and processing parameters set forth hereinbefore for pore volume adjustment. Density of the absorbent foam structures herein need not be uniform throughout the structure. Some portions or zones of the foam structure may have relatively higher or lower densities than other portions or zones thereof.

2) Cell Size

Another alternative or supplemental structural feature of the absorbent foams herein, which is not an essentially established parameter but which may be useful in defining preferred foam materials of this invention, is cell size. Foam cells, and especially cells which are formed by polymerizing a monomer-containing oil phase that surrounds relatively monomer-free water-phase bubbles, will frequently be substantially spherical in shape. The size or "diameter" of such substantially spherical cells is thus yet another commonly utilized parameter for characterizing foams in general as well as for characterizing certain preferred absorbent foams of the type utilized in the present invention. Since cells in a given sample of polymeric foam will not necessarily be of approximately the same size, an average cell size, i.e., average cell diameter, will often be specified.

As with foam density, capillary suction specific surface area and pore volume, cell size is a foam parameter which can also impact on a number of important mechanical and performance features of the absorbent foam material of this invention. Since cell size is a factor, along with capillary suction specific surface area, pore volume and foam hydrophilicity, that determines the capillarity of the foam, cell size is a foam structure parameter that can directly affect both the absorbent capacity and the internal fluid wicking properties of the foam absorbents herein. Cell size can also affect mechanical properties of the foam absorbents herein including such features as flexibility and resistance to and recovery from compression deflection.

A number of techniques are available for determining average cell size in foams. These techniques include mercury porosimetry methods which are well known in the art. The most useful technique, however, for determining cell size in foams involves simple photographic measurement of a foam sample. FIG. 1 of the drawings, for example, is a photomicrograph of a fracture surface of a typical HIPE foam absorbent structure of the present invention. Superimposed on the photomicrograph is a scale representing a dimension of 10 microns. Such a scale can be used to determine average cell size via an image analysis procedure. Image analysis of photomicrographs of foam samples is, in fact, a commonly employed analytical tool which can be used to determine average cell size of the foam structures herein. Such a technique is described in greater detail in Edwards et al; U.S. Pat. No. 4,788,225; Issued Nov. 29, 1988. This patent is incorporated herein by reference.

As determined by direct photographic measurement, the foams useful as absorbents for aqueous body fluids in accordance with the present invention will preferably have an average cell size ranging from about 5 to 100 microns. More preferably, cell size will range from about 10 to 90 microns. Most preferably, cell size will be between about 15 and 80 microns.

Size or diameter of the cells in the foam absorbents herein can be influenced and controlled by variation of the same type of foam composition and processing features that influence capillary suction specific surface area and available pore volume. For the preferred HIPE-based foams, these include primarily those factors which determine the size of the water-phase "bubbles" in the HIPE emulsion precursor of the polymeric foam structures herein. Thus, cell size can be varied by adjusting water-to-oil ratio of the HIPE emulsion, and the type and amount emulsifier used to form the HIPE emulsion. Cell size may also be altered by simply compressing the solid foam structures after they have been prepared.

As indicated hereinbefore, the dimensions of cells in the absorbent foams of this invention will generally not be uniform so an average cell size for any given foam sample or zone in a foam sample can and should be calculated. It is, of course, possible to utilize absorbent foams which have discrete, identifiable zones of relatively larger or relatively smaller average cell size.

II) MECHANICAL FEATURES

Absorbent foams having suitable polymeric composition and the structural features hereinbefore described will, in general, possess mechanical properties, e.g., resistance to compression deflection, flexibility, recovery from compression deflection, integrity, softness, etc., which render such foams suitable for use as absorbent structures in absorbent articles such as disposable diapers. Within the aforementioned structural limitations, however, it is possible to select certain combinations of parameters and/or certain foam preparation techniques and conditions which provide foam absorbents that exhibit especially desirable mechanical properties. The specific, somewhat interrelated mechanical properties which have been identified as contributing to the realization of absorbent foams especially suitable for use in absorbent articles for incontinence management can be summarized as follows:

A) Resistance to Compression Deflection

The most important mechanical feature of the polymeric foams of this invention is the strength of the foam absorbent as determined by its resistance to compression deflection. The resistance to compression deflection exhibited by the foam absorbents herein is a function of the polymer elastic modulus and the dimensions of the "struts" which form the foam network. The elastic modulus of the struts is, in turn, determined by a) the polymeric composition of the struts and b) the extent to which the struts may be plasticized by residual material, e.g., emulsifiers, synthesis water phase or subsequently added hydrophilizing agents, left in the foam structure after processing.

To be useful as absorbent structures in absorbent articles such as diapers, the absorbent foam materials of the present invention must be suitably resistant to deformation or compression by forces encountered when such absorbent materials are engaged in the absorption and retention of fluids. Foams which do not possess sufficient foam strength in terms of resistance to compression deflection may be able to acquire and store acceptable amounts of body fluid under no-load conditions but will too easily give up such fluid under the compressive stress caused by the motion and activity of the wearer of the absorbent articles which contain the foam.

The resistance to compression deflection exhibited by the foam absorbents used in the present invention can be quantified by determining the amount of strain produced in a sample of saturated foam material held under a certain confining pressure for a specified period of time. For purposes of the present invention such measurements can be made on a foam sample of standard size (cylinders which are 0.8 cm thick and have a cross-sectional circular area of 6.5 cm$^2$). Such samples are saturated with synthetic urine having a surface tension of 65±5 dynes/cm and are thereafter subjected to a confining pressure of 5.1 kPa for a period of 15 minutes at a temperature of 37° C. The amount of strain produced in such testing is reported as a percentage of the original sample thickness that the compressed thickness of the sample represents. The method for carrying out this particular type of test for quantifying resistance to compression deflection is set forth hereinafter in greater detail in the TEST METHODS section.

The absorbent foams useful herein are those which exhibit a resistance to compression deflection such that a confining pressure of 5.1 kPa produces a strain of from about 5% to 95% compression of the foam structure when it has been saturated to its free absorbent capacity with synthetic urine having a surface tension of 65±5 dynes/cm. Preferably the strain produced under such conditions will range from about 5% to 75%, most preferably from about 5% to 50%. For the preferred HIPE foams of this invention, resistance to compression deflection can be adjusted to strain values within the foregoing ranges by appropriate selection of monomer, comonomer and cross-linker types and concentrations in combination with selection of appropriate emulsion formation and emulsion polymerization conditions and techniques. Thus, such preferred foams can be formed from materials with elastic modulii large enough to provide adequate resistance to compression deflection even though such foams are low density and have very fine struts to provide high specific surface area.

B) Flexibility

The absorbent foams of the present invention must be sufficiently flexible so that they can be utilized in absorbent products that will conform to the body shape of the wearer. Characterization of the absorbent foams herein as flexible, therefore, means that these foams can be deformed or bent to the extent necessary for use in such absorbent articles without significant damage to their structural integrity or significant loss of their absorbent properties.

Preferred absorbent foams of the present invention must also be sufficiently flexible to withstand compressive or deforming forces which are encountered during preparation, processing, packaging, shipping and storing of absorbent articles containing such foam materials. Disposable diapers, for example, are generally packaged and marketed in a folded condition wherein the diaper core is folded in both the longitudinal and transverse directions. Disposable diapers are also generally marketed in the form of stacks of folded diapers, which stacks are contained and compressed by their surrounding packaging. Accordingly, the compressive and deforming forces to which the foam absorbents herein may be subjected during processing and marketing may be even greater than those which are applied to the foam materials in use.

Given the nature of treatment which the absorbent foams herein must withstand, preferred absorbent foam materials of this invention will possess flexibility characteristics which can be quantified by referencing their ability to withstand bending without undergoing significant damage to their structural integrity. Described in the TEST METHODS section hereinafter is a procedure for determining the flexibility of the absorbent foams herein by determining whether and how many times a foam sample of a given specified size can be bent around a cylindrical mandrel at a specified rate without breaking. The preferred foams of this invention are those which are flexible enough so that, at their point of use as an absorbent for body fluids, the saturated foam material at 37° C. can be subjected to this bending test without breaking (i.e., exhibit a bending value of at least one cycle). More preferably, preferred foams can be bent at least 2 times, even more preferably at least 5 times without breaking when subjected to such a test procedure.

C) Preferred or Supplemental Mechanical Properties

In addition to their resistance to compression deflection and flexibility characteristics, the preferred foam absorbents of the present invention will also possess several additional types of mechanical attributes. These preferred mechanical attributes include desirable recovery from compression deflection (i.e., resilience), foam integrity, and softness to the touch. Each of these preferred mechanical properties is described in greater detail as follows:

1) Recovery From Compression Deflection

Recovery from compression deflection relates to the tendency or propensity of a piece of foam material to return to its original dimensions after being deformed or compressed under forces encountered in manufacture, storage or use. For purposes of the present invention, recovery from compression deflection of the preferred foam absorbents herein should be determined on foams which are at their appropriate point-of-use density, and frequently under such conditions, the foam will contain absorbed body fluid. Accordingly, recovery from compression deflection may be measured on foams which are either dry or saturated with synthetic urine.

A suitable procedure for determining recovery from compression deflection is set forth in the TEST METHODS section hereinafter. Such a procedure in general involves compression and release of a standard size foam sample which is either dry or has been saturated to its free absorbent capacity with synthetic urine. Samples are maintained under 50% compression for a set period of time and then are released from compression. The extent to which the sample recovers its thickness in the one-minute period after the release of compressive force is taken as a measure of the recovery from compression deflection (resilience) propensity of the sample.

Preferred absorbent foams of the present invention will generally exhibit a recovery of at least 85% of original caliper when dry and/or at least 75% of original caliper when wet after one minute. More preferably, such preferred foam materials will have a recovery from compression deflection of at least 90% dry and/or 80% wet.

2) Foam Integrity and Softness

While not absolutely essential for the realization of operable or useful absorbent structures, the HIPE foam absorbents of this invention will preferably possess the additional mechanical attributes of structural integrity in use and softness (lack of irritation) to the touch. For example, foam materials that will be employed in such absorbent articles as infant diapers will frequently be subjected to both dynamic and static forces which arise when the wearer walks, runs, crawls or jumps. Such forces may not only tend to compress the foam absorbents and expel fluid therefrom, but such forces may also tend to rip or tear or otherwise fragment the foam structure. Obviously, it would be advantageous for foam structures which are to be used in this manner to have sufficient structural integrity to minimize the incidence of foam tearing or fragmenting in use.

The foam elements of this invention may also be used in absorbent articles, as described more fully hereinafter, in configurations wherein the foam material surface may come in close proximity to or even in actual contact with the wearer's skin. Accordingly, it would be very desirable for the surface of the foam absorbents herein to be acceptably soft and non-irritating to the touch.

III) FLUID HANDLING AND ABSORBENCY CHARACTERISTICS

Absorbent foams having suitable polymeric composition, and the structural characteristics and mechanical features as hereinbefore described, will in general exhibit especially desirable and useful body fluid handling and absorbency characteristics. Such fluid handling and absorbency characteristics are in turn the attributes of the preferred foam materials herein which render such foams especially suitable for use as absorbent structures in absorbent articles designed to acquire and hold aqueous body fluids.

The fluid handling and absorbency characteristics which are most relevant to the realization of suitable absorbent foams are, A) the equilibrium absorbent capacity of the foam, especially under pressure, B) the rate of vertical wicking of fluid through the foam structure, C) the absorbent capacity of the foam at specific reference wicking heights, and D) the ability of the absorbent foam structures to drain (partition) fluid from competing absorbent structures with which the foam may be in contact. Each of these characteristics is described in greater detail as follows:

A) Absorbent Capacity and Absorbent Capacity Under Pressure

Absorbent capacity is the total amount of test fluid (synthetic urine) which a given foam sample will absorb into its cellular structure per unit mass of solid material in the sample. Absorbent capacity under pressure refers to the amount of that fluid held under no confining pressure (free capacity) which the foam will retain within its cellular structure when the foam sample is subjected to compressive force. Such absorbent capacity measurements are for purposes herein calculated at equilibrium, i.e., after the foam sample has been allowed to acquire and/or hold all of the fluid it can over whatever time period is needed to form a completely saturated foam sample with test liquid. The foam materials which are especially useful as absorbents in absorbent articles such as diapers will exceed a minimum free absorbent capacity and will also exceed a minimum absorbent capacity under pressure.

Using the procedure described in greater detail hereinafter in the TEST METHODS section, free absorbent capacity and absorbent capacity under pressure can both be determined for any given foam sample by a gravimetric analysis technique. In such a technique, a foam sample of specified known size and weight is placed in a dish of test fluid (synthetic urine) and is allowed to absorb the test fluid to equilibrium. After removal of the saturated sample from the fluid, the amount of fluid held per gram of foam, i.e., the measured free capacity, is then calculated. This saturated foam sample is then subjected in step wise fashion to increasing compressive pressure in several increments with the expressed fluid being drained away at each step. The amount of fluid retained in the sample at each pressure loading up to about 1.0 psi (6.9 kPa) is determined gravimetrically.

To be especially useful in absorbent articles for absorbing urine, the foam absorbents of the present invention should have an equilibrium free capacity of at least about 12, and preferably at least about 20, mL of synthetic urine per gram of dry foam material. Furthermore the capacity of such foam materials under a confining pressure of about 0.74 psi (5.1 kPa) maintained for 15 minutes at 37° C. should be at least about 5%, more preferably at least about 20%, of the equilibrium free capacity of such foams.

B) Vertical Wicking Performance

Yet another fluid handling attribute of the absorbent foams useful herein relates to their ability to quickly move or "wick" acceptable amounts of body fluids through their foam structures. Vertical wicking, i.e., fluid wicking in a direction opposite from gravitational force, is an especially desirable performance attribute for the absorbent foam materials herein. This is because such materials will frequently be utilized in absorbent articles in a manner that fluid to be absorbed must be moved within the article from a relatively lower position to a relatively higher position within the absorbent core of the article.

Vertical wicking performance is related to the magnitude of the capillary suction driving force which moves liquid through the foam and holds it in the foam structure. Foam characterizing parameters which relate to vertical wicking propensity thus provide an indication as to how well preferred foams herein will perform as absorbent structures in absorbent articles. For the foam absorbents of the present invention, fluid wicking propensity can be quantified by referencing both a vertical wicking rate test and a vertical wicking absorbent capacity test.

1) Vertical Wicking Rate

The vertical wicking rate test measures the time taken for a colored test liquid (e.g., synthetic urine) from a reservoir to wick a vertical distance of 5 cm through a test strip of foam of specified size when the test is performed at 37° C. Such a vertical wicking rate test is described in greater detail in the TEST METHODS section hereinafter. To be especially useful in absorbent articles for absorbing urine, the foam absorbents of the present invention will preferably have a 5 cm vertical wicking rate of no more than about 30 minutes when wicking synthetic urine (65±5 dynes/cm). More preferably, the preferred foam absorbents of the present invention will have a 5 cm vertical wicking rate of no more than about 5 minutes when wicking synthetic urine.

2) Vertical Wicking Absorbent Capacity

The vertical wicking absorbent capacity test is carried out in conjunction with the vertical wicking rate test. Vertical wicking absorbent capacity measures the amount of test fluid per gram of absorbent foam that is wicked to each one inch (2.54 cm) vertical section of the same standard size foam sample used in the vertical wicking rate test. Such a determination is generally made after the sample has been allowed to vertically wick test fluid to equilibrium (e.g, after about 18 hours). Like the vertical wicking rate test, the vertical wicking absorbent capacity test is described in greater detail hereinafter in the TEST METHODS section.

To be especially useful in absorbent articles for absorbing urine, the preferred foam absorbents of the present invention will generally have a vertical wicking absorbent capacity such that, at 11.4 cm (4.5 inches) of vertical wicking height, the foam test strip has an absorbent capacity of at least about 10 mL of synthetic urine (65±5 dynes/cm) per gram of absorbent foam. More preferably, the preferred foam absorbents herein will have a vertical wicking absorbent capacity at 11.4 cm (4.5 inches) of from about 20 to 45 mL of synthetic urine per gram of foam.

C) Partitioning

The absorbent foam structures herein will frequently be utilized in absorbent articles along with other types of absorbent structures which may also participate in acquiring, distributing and/or storing discharged body fluids. In those contexts wherein the foam structures herein are to serve primarily as a fluid storage/redistribution component in absorbent articles, it is desirable for such foams to have a propensity for pulling body fluids into the foam structure from other absorbent components which also are absorbing such fluids. Such a propensity to drain fluid from other absorbent article components is known in the art as "partitioning." The concept of partitioning and certain procedures for determining partitioning performance are described, for example, in Weisman/Goldman; U.S. Pat. No. 4,610,678; Issued Sep. 9, 1986. When tested for partitioning performance using procedures similar to those disclosed in U.S. Pat. No. 4,610,678, the absorbent foam structures of this invention exhibit especially desirable fluid partitioning characteristics.

IV) PREFERRED HIPE ABSORBENT FOAMS

As noted hereinbefore, especially preferred absorbent foam materials which can be prepared to have both the requisite and preferred structural, mechanical and fluid handling characteristics as hereinbefore described are the products which result from polymerization of certain water-in-oil emulsions having therein a relatively high ratio of water phase to oil phase. Emulsions of this type which have these relatively high water to oil phase ratios are known in the art as high internal phase emulsions ("HIPEs" or "HIPE" emulsions). The preferred polymeric foam materials which result from the polymerization of such emulsions are referred to herein as "HIPE foams."

The relative amounts of the water and oil phases used to form the polymeric foam precursor HIPE emulsions are, among many other parameters, important in determining the structural, mechanical and performance properties of the resulting preferred polymeric foams. In particular, the ratio of water to oil in the foam-forming emulsion can influence foam density, cell size, specific surface area of the foam and dimensions of the struts which form the foam. The emulsions used to prepare the preferred polymeric HIPE foam materials of this invention will generally have water-to-oil phase ratios ranging from about 12:1 to 100:1; more preferably from about 20:1 to 70:1; most preferably from about 25:1 to 50:1.

The continuous oil phase of the emulsions used to prepare the preferred HIPE foams herein comprises the monomers that are to be polymerized to form the solid foam structure. Such monomers include a principal monomer component, a comonomer component and a cross-linking agent component. Selection of particular types and amounts of monofunctional principal monomer(s) and comonomer(s) and polyfunctional cross-linking agent(s) can be important to the realization of absorbent HIPE foam materials having the desired combination of structure, mechanical, and fluid handling properties which render such materials suitable for use in the invention herein.

The principal monofunctional monomer component utilized in the oil phase of the preferred foam-precursor HIPE emulsions comprises one or more monomers that tend to impart glass-like properties to the eventually resulting foam structure. Such monomers are hereinafter referred to as "glassy" monomers, and are, for purposes of this invention, defined as monomeric materials which would produce high molecular weight (greater than 6000) homopolymers having a glass transition temperature, $T_g$, above about 40° C. The preferred monofunctional glassy monomer type is a styrene-based monomer with styrene itself being the most preferred monomer of this kind. Substituted, e.g., monosubstituted, styrene such as p-methylstyrene may also be employed. The monofunctional glassy monomer component will normally comprise from about 3% to 41%, more preferably from about 7% to 40% by weight of the oil phase used to form the HIPE emulsion to be polymerized.

The monofunctional comonomer component, which will also be present in the oil phase of the HIPE emulsion along with the glassy principal monomer material, comprises one or more comonomers which tend to impart rubber-like properties to the eventually resulting foam structure. Such comonomers are hereinafter referred to as "rubbery" comonomers and are, for purposes of this invention, defined as monomeric materials which would produce high molecular weight (greater than 10,000) homopolymers having a glass transition temperature, $T_g$, of about 40° C. or lower. Monofunctional rubbery comonomers of this type include, for example, alkyl-acrylates, alkylmethacrylates, allylacrylate, butadiene, substituted butadienes, vinylidine halides and combinations of such comonomers and comonomer types. Preferred rubbery comonomers include butylacrylate, 2-ethylhexylacrylate, butadiene, isoprene and combinations of these comonomers. Of all of these species, butylacrylate and 2-ethylhexylacrylate are the most preferred. The monofunctional rubbery comonomer component will generally comprise from about 27% to 73%, more preferably from about 27% to 66%, by weight of the oil phase.

In the HIPE emulsions used to form the preferred absorbent foams herein, both the monofunctional glassy principal monomer(s) and the monofunctional rubbery comonomer(s) must be present in the oil phase within the hereinbefore recited concentration ranges. In addition, the molar ratio of monofunctional glassy monomer component to the monofunctional rubbery component will generally range from about 1:25 to 1.5:1, more preferably from about 1:9 to 1.5:1.

Since the polymer chains formed from the glassy monomer(s) and the rubbery comonomer(s) are to be cross-linked, the oil phase of the emulsions used to form the preferred HIPE foams herein must also contain a polyfunctional cross-linking agent. As with the monofunctional monomers and comonomers, selection of a particular type and amount of cross-linking agent is very important to the eventual realization of preferred polymeric foams having the desired combination of structural, mechanical, and fluid-absorbing properties.

Depending upon the type and amounts of monofunctional monomers and comonomers utilized, and depending further upon the desired characteristics of the eventually realized preferred polymeric foams, the polyfunctional cross-linking agent component for use in the preferred HIPE emulsion foam precursor can be selected from a wide variety of polyfunctional, preferably difunctional, monomers. Thus, the cross-linking agent may be a divinyl aromatic material such as divinylbenzene, divinyltolulene or diallylphthalate. Alternatively, divinyl aliphatic cross-linkers such as any of the diacrylic acid esters of polyols can be utilized. The cross-linking agent found to be suitable for preparing the most acceptable foam from the preferred HIPE emulsions herein is divinylbenzene.

The cross-linking agent of whatever type will generally be employed in the oil phase of the preferred foam-forming emulsions herein in an amount of from about 8% to 40%, more preferably from about 10% to 25%, by weight. Amounts of cross-linking agent(s) within such ranges will generally provide a cross-linker molar concentration of from about 5 mole percent to about 60 mole percent, based on total monomers present in the oil phase.

The major portion of the oil phase of the preferred HIPE emulsions herein will comprise the aforementioned monomers, comonomers and cross-linking agents which eventually form the preferred polymeric foam absorbents. It is therefore essential that these monomers, comonomers and cross-linking agents be substantially water-insoluble so that they are primarily soluble in the oil phase and not the water phase. Use of such substantially water-insoluble monomer materials ensures that preferred HIPE emulsions of appropriate characteristics and stability will be realized.

It is, of course, highly preferred that the monomers, comonomers and cross-linking agents used to form the preferred polymeric foam materials herein be of the type such that the eventually formed foam polymer is suitably non-toxic and appropriately chemically stable. Thus such monomers, comonomers and cross-linking agents should preferably have little or no toxicity in the very low residual concentrations wherein they may be encountered during post-polymerization foam processing and/or use.

Another essential component of the oil phase of the HIPE emulsions used to form the preferred polymeric foams of the present invention comprises an emulsifier which permits formation of stable HIPE emulsions. Such emulsifiers are those which are soluble in the oil phase used to form the emulsion. Emulsifiers utilized may be nonionic, cationic, anionic or amphoteric provided the emulsifier or combination of emulsifiers will form a stable emulsion. Preferred types of emulsifiers which can be used to provide an emulsifier component having suitable characteristics include the sorbitan fatty acid esters, polyglycerol fatty acid esters, polyoxyethylene (POE) fatty acids and esters. Especially preferred are the sorbitan fatty acid esters such as sorbitan monolaurate (SPAN ® 20), sorbitan monooleate (SPAN ® 80) and combinations of sorbitan trioleate (SPAN ® 85) and sorbitan monooleate (SPAN ® 80). One such particularly preferred emulsifier combination comprises the combination of sorbitan monooleate and sorbitan trioleate in a weight ratio greater than or equal to about 3.1, more preferably about 4:1. Other operable emulsifiers include TRIODAN ® 20 which is a commercially available polyglycerol ester marketed by Grindsted and EMSORB 2502 which is a sorbitan sesquioleate marketed by Henkel.

The emulsifier component will generally comprise from about 2% to 33% by weight of the oil phase used to form the HIPE emulsions which in turn are used to prepare the preferred polymeric foams herein. More preferably, the emulsifier component will comprise from about 4% to 25% by weight of the oil phase.

In addition to the monomeric and emulsifier components hereinbefore described, the oil phase used to form polymerizable HIPE emulsions herein may also contain additional optional components. One such optional oil phase component may be an oil soluble polymerization initiator of the general type hereinafter described. Another possible optional component of the oil phase may be a substantially water insoluble solvent for the oil phase monomer and emulsifier components. A solvent of this type must, of course, not be capable of dissolving the eventually polymerized monomers. Use of such a solvent is not preferred, but if such a solvent is employed, it will generally comprise no more than about 10% by weight of the oil phase.

As indicated, the HIPE oil phase as hereinbefore described is the continuous phase in the emulsions to be polymerized to realize the preferred foams of the present invention. The discontinuous internal phase of the polymerizable HIPE emulsions is the water phase which will generally be an aqueous solution containing one or more dissolved components. One essential dissolved component of the water phase is a water-soluble electrolyte. The dissolved electrolyte in the water phase of the HIPE emulsion serves to minimize the tendency of monomers and crosslinkers which are primarily oil soluble to also dissolve in the water phase. This, in turn, can minimize the extent to which, during polymerization of the emulsion, polymeric material fills the cell windows at the oil/water interfaces formed by the water phase bubbles. Thus the presence of electrolyte and the resulting ionic strength of the water phase can determine whether and to what degree the resulting preferred polymeric foams may be open-celled.

Any electrolyte which provides ionic species to impart ionic strength to the water phase may be used. Preferred electrolytes are mono-, di-, or tri-valent inorganics salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in these preferred embodiments of the present invention.

Generally electrolyte will be utilized in the water phase of the HIPE emulsions which are precursors to the preferred polymeric foams herein in a concentration which ranges from about 0.2% to about 40% by weight of the water phase. More preferably, the electrolyte will comprise from about 0.5% to 20% by weight of the water phase.

The HIPE emulsions used to prepare the preferred polymeric foams herein will also typically contain a polymerization initiator. Such an initiator component is generally added to the water phase of the HIPE emulsions and can be any conventional water-soluble free radical initiator. Materials of this type include peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts.

The initiator material can comprise up to about 5 mole percent based on the total moles of polymerizable monomers present in the oil phase. More preferably, the initiator comprises from about 0.001 to 0.5 mole percent based on the total moles of polymerizable monomers in the oil phase. When used in the water-phase, such initiator concentrations can be realized by adding initiator to the water phase to the extent of from about 0.02% to 0.4%, more preferably from about 0.1% to 0.2% by weight of the water phase.

Via a process described more fully hereinafter, the oil and water phases as hereinbefore described are combined under agitation to form an emulsion in the form of a stable foam. This HIPE foam is then subjected to polymerization conditions which are sufficient and suitable to bring about polymerization of the monomers in the oil phase and to thereby form a solid cellular foam structure.

The chemical nature, makeup and morphology of the polymer material which forms the foam structures herein is determined by both the type and concentration of the monomers, comonomers and crosslinkers utilized in the HIPE emulsion and by the emulsion polymerization conditions employed. Such polymeric material will generally be non-swellable in aqueous liquids in that the material itself does not significantly plasticize or imbibe aqueous liquids it contacts. However, no matter what the particular monomeric makeup, molecular weight or morphology of the polymeric material might be, the resulting preferred polymeric material will generally be viscoelastic in character. Thus the polymer of the preferred foam structures herein will possess both viscous, i.e., fluid-like, properties and elastic, i.e., spring-like, properties. It is important that the polymeric material which forms the cellular foam structure have physical, rheological, and morphological attributes which, under conditions of use, impart suitable flexibility, resistance to compression deflection, and dimensional stability to the absorbent foam material.

The cross-linked polymer material that forms the preferred absorbent foam structures herein will preferably be substantially free of polar functional groups on its polymeric structure. Thus, immediately after the polymerization step, the polymer material which forms the foam structure surfaces of such preferred absorbent foams will normally be relatively hydrophobic in character. Accordingly, preferred just-polymerized foams may need to be further treated to render the foam structure surfaces relatively more hydrophilic so that such foams can be used as absorbents for aqueous body fluids. Hydrophilization of the foam surfaces, if necessary, can generally be accomplished by treating the HIPE foam structures as polymerized with a hydrophilizing agent in a manner described more fully hereinafter.

Hydrophilizing agents are any materials which will enhance the water wettability of the polymeric surfaces with which they are contacted and onto which they are deposited. Hydrophilizing agents are well known in the art. Such known agents will generally include surfactant materials of the anionic, cationic or nonionic type. Hydrophilizing agents will generally be employed in liquid form, typically dissolved in water to form an aqueous hydrophilizing solution which is applied to the HIPE foam surfaces. In this manner, hydrophilizing agents can be adsorbed to the polymeric surfaces of the preferred HIPE foam structures in amounts suitable for rendering such surfaces substantially hydrophilic but without altering the desired flexibility and compression deflection characteristics of the foam. In preferred foams which have been treated with hydrophilizing agents, hydrophilizing agent is incorporated into the foam structure such that residual amounts of the agent which remain in the foam structure range from about 0.1% to 10% by weight of the foam.

One type of suitable hydrophilizing agent comprises mild, non-irritating surfactants applied to the foam structure in amounts sufficient to provide residual surfactant in the foam to the extent of from about 0.5% to 5.0% by weight, more preferably from about 1% to 3% by weight, based on the weight of the foam. Such surfactants can include, for example, alkyl sulfates and alkylethoxylated sulfates of the type utilized in commercially marketed dishwashing liquids such as JOY LIQUID DETERGENT. Aqueous solutions of such surfactants are typically used to wash the HIPE foam structure, either after removal of the residual water phase material left from the foam polymerization operation or, more preferably, as part of the washing treatment that serves to remove this residual water phase material.

Another preferred type of hydrophilizing agent comprises hydratable, and preferably hygroscopic or deliquesent, water soluble inorganic salts. Such materials include, for example, toxicologi-cally acceptable alkaline earth metal salts. Materials of this type and their use in conjunction with water-insoluble surfactants as foam hydrophilizing agents are described in greater detail in the U.S. patent application of Thomas A. DesMarais having Ser. No. 07/743,951, concurrently filed herewith and incorporated herein by reference. Preferred salts of this type include the calcium and magnesium halides such as calcium chloride which, as noted hereinafter, may also be employed as the electrolyte in the water phase of the HIPE emulsions used to prepare preferred absorbent foams.

Hydrophilizing agents in the form of hydratable inorganic salts can easily be incorporated into the absorbent foams herein by treating the foams with aqueous solutions of such salts. As with surfactant hydrophilizing agents, solutions of hydratable inorganic salts can generally be used to treat and hydrophilize hydrophobic foams after completion of, or as part of, the process of removing the residual water phase from the just-polymerized foams. Contact of foams with such solutions is preferably used to deposit hydratable inorganic salts such as calcium chloride in residual amounts which range from about 0.1% to 7% by weight of the foam.

Hydrophilizing treatment of those of the preferred foam structures which are relatively hydrophobic as polymerized will typically be carried out to the extent that is necessary and sufficient to impart suitable hydrophilicity to the preferred HIPE foams of the present invention. Some foams of the preferred HIPE emulsion type, however, may be suitably hydrophilic as prepared and thus may need no additional treatment with hydrophilizing agents. In particular, such preferred HIPE foams may be those wherein sorbitan fatty acids esters are used as emulsifiers added to the oil phase and calcium chloride is used as an electrolyte in the water phase of the HIPE emulsion foam precursors. In that instance, residual water-phase liquid held within the foams after polymerization may contain or deposit sufficient amounts of calcium chloride to render the residual-emulsifier-containing internal foam surfaces suitably hydrophilic even after the polymerized-emulsion foams have been dewatered.

V) ABSORBENT FOAM PREPARATION METHODS

The absorbent foam materials of the present invention can be prepared using any suitable polymerization and post-polymerization process steps and using any suitable combination of monomeric materials, so long as hydrophilic foams result which have the hereinbefore described essential, and if desired preferred, structural and mechanical characteristics. As noted, a preferred method of realizing polymeric foams having the requisite structural and mechanical characteristics, and having the desired fluid handling properties, involves the polymerization of High Internal Phase Emulsions (HIPEs). Preparation of absorbent foams using this preferred procedure will thus be described to illustrate how foams of the type envisioned herein can be made.

This preferred foam preparation method involves the steps of, A) forming a stable high internal phase emulsion (HIPE), B) thereafter polymerizing this stable emulsion under conditions suitable for forming a solid polymeric foam structure, C) washing and, if necessary, hydrophilizing the solid polymeric foam structure by treating the structure with water and/or liquid-form hydrophilizing agents to remove the original residual water phase from the polymeric foam structure and to deposit any needed hydrophilizing agent, and D) thereafter dewatering this polymeric foam structure to the extent necessary to render the foam material useful as an absorbent for aqueous body fluids. Each of these basic process steps is described in greater detail as follows:

A) Formation of HIPE Emulsion

The HIPE emulsion precursor to the preferred foam absorbent materials herein can be formed by combining an oil phase as hereinbefore described with a water phase also as hereinbefore described. The weight ratio of the water phase to the oil phase and such a combination will generally range from about 12:1 to 100:1, more preferably from about 20:1 to 70:1.

The oil phase used to form the HIPE emulsions herein will contain the hereinbefore specified essential components such as the requisite monomers, comonomers, cross-linkers and emulsifiers. The oil phase may also contain optional components such as solvents and polymerization initiators. The water phase used to form the HIPE emulsions herein will contain the hereinbefore specified electrolyte as an essential component and may also contain optional components such as water-soluble emulsifiers, and/or polymerization initiators.

The HIPE emulsion can be formed from the combined oil and water phase by subjecting this combination of phases to shear agitation. Shear agitation is generally applied to the extent and for a time period necessary to form a stable emulsion from the combined oil and water phases. Such a process may be conducted in either batchwise or continuous fashion and is generally carried out under conditions suitable for forming an emulsion wherein the oil phase droplets are dispersed to such an extent that the polymerized foam which is eventually formed from the emulsion will have the requisite pore volume and other structural characteristics. Emulsification of the oil and water phase combination will frequently involve the use of a mixing or agitation device such as a pin impeller.

One preferred method of forming HIPE emulsions which can be employed herein involves a continuous process for combining and emulsifying the requisite oil and water phases. In such a process, a liquid stream comprising the oil phase as hereinbefore described is formed and provided at a flow rate ranging from about 0.08 to 1.5 mL/sec. Concurrently, a liquid stream comprising the water phase as hereinbefore described is also formed and provided at a flow rate ranging from about 4 to 5 g mL/sec. At flow rates within the foregoing ranges, these two streams are then combined in a suitable mixing chamber or zone in a manner such that the requisite water to oil phase weight ratios as hereinbefore set forth are approached, reached and maintained.

In the mixing chamber or zone, the combined streams are generally subjected to shear agitation as provided, for example, by a pin impeller of suitable configuration and dimensions. Shear will typically be applied to the extent of from about 1000 to 4000 sec.$^{-1}$. Residence times in the mixing chamber will frequently range from about 5 to 30 seconds. Once formed, the stable HIPE emulsion in liquid form can be withdrawn from the mixing chamber or zone at a flow rate from about 4 to 52 mL/sec.

This preferred method for forming useful HIPE emulsions via a continuous process is described in greater detail in the U.S. patent application of Thomas A. DesMarais, Stephen T. Dick and Thomas M. Shiveley having Ser. No. 07/743,947 (now abandoned). This application, which is concurrently filed herewith, is incorporated herein by reference.

B) Polymerization of the HIPE Emulsion

The HIPE emulsion, formed as described hereinbefore, will generally be placed in a suitable reaction vessel, container or region to be polymerized. In one embodiment herein, the reaction vessel comprises a tub constructed of polyethylene from which the eventually polymerized solid foam material can be easily removed for further processing after polymerization has been carried out to the extent desired.

Polymerization conditions to which the HIPE emulsion will be subjected will vary depending upon the monomeric and other makeup of the oil and water phases of the emulsion and the type and amounts of polymerization initiators utilized. Frequently, however, polymerization conditions will comprise maintenance of the HIPE emulsion at elevated temperatures of from about 55° C. to 90° C., more preferably from about 60° C. to 66° C., for a time period ranging from about 4 to 24 hours, more preferably from about 4 to 12 hours.

C) Washing and Hydrophilizing of the HIPE Foam

The solid HIPE foam which is formed upon completion of the hereinbefore described polymerization step will generally be a flexible, open-cell porous structure having its cells filled with the residual water phase material which was used to prepare the HIPE emulsion prior to polymerization. This residual water phase material, which generally comprises an aqueous solution of electrolyte, residual emulsifier, and polymerization initiator, should be removed from the foam structure at this point prior to further processing and use of the foam. Removal of the original water phase material will usually be carried out by compressing the foam structure to squeeze out residual liquid and/or by washing the foam structure with water or other aqueous washing solutions. Frequently several compressing and washing steps, e.g., 2 cycles, will be utilized.

After the original water phase material has been removed from the foam structure to the extent required, the HIPE foam may need to be treated, i.e., by continued washing, with an aqueous solution of a suitable hydrophilizing agent. Hydrophilizing agents which may be employed are listed hereinbefore. As noted, treatment of the HIPE foam structure with the hydrophilizing agent solution continues, if necessary, until the desired amount of hydrophilizing agent has been incorporated and until the foam exhibits a desired adhesion tension value for any test liquid of choice.

D) Foam Dewatering

After the HIPE foam has been treated to the extent necessary to render the eventually dried foam suitably hydrophilic, the foam will generally be dewatered prior to being cut or otherwise made ready for use as an absorbent structure in an absorbent article. Dewatering can be brought about by compressing the foam to squeeze out residual water, by subjecting the foam, or the water therein, to elevated temperatures, e.g., to temperatures from about 60° C. to 200° C. or to microwave treatment, or by a combination of both compressing and water heating techniques. The dewatering step of HIPE foam processing will generally be carried out until the HIPE foam ready for use is as dry as practical. Frequently such compression dewatered foams will have a water (moisture) content of from about 50% to 500%, more preferably from about 50% to 200%, by weight on a dry weight basis. Subsequently, heated foams can be dried to a moisture content of from about 5% to 40%, more preferably from about 5% to 15%, on a dry weight basis.

VI) ABSORBENT ARTICLES

The present invention also relates to body fluid absorbing articles which utilize the foam absorbent structures herein as at least a portion-of their fluid-absorbing "core" element. By "absorbent article" herein is meant a consumer product which is capable of absorbing significant quantities of urine or other fluids (i.e., liquids), like aqueous focal matter (runny bowel movements), discharged by an incontinent wearer or user of the article. Examples of such absorbent articles include disposable diapers, incontinence garments, disposable training pants, bed pads, and the like. The absorbent foam structures herein are particularly suitable for use in articles like diapers, incontinence pads or garments, clothing shields and the like.

In its simplest form, an absorbent article of the present invention need only include a relatively liquid-impervious backing sheet and one or more foam absorbent structures associated with this backing sheet. The foam absorbent and the backing sheet will be associated in such a manner that the foam absorbent structure material is situated between the backing sheet and the fluid discharge region of the wearer of the absorbent article. Liquid impervious backing sheets can comprise any material, for example polyethylene or polypropylene, having a caliper of about 1.5 mils (0.038 mm), which will help retain fluid within the absorbent article.

More conventionally, the absorbent articles herein will also include a liquid-pervious topsheet element which covers the side of the absorbent article that touches the skin of the wearer. In this configuration, the article includes an absorbent core comprising one or more foam absorbent structures of the present invention positioned between the backing sheet and the topsheet. Liquid-pervious topsheets can comprise any material such as polyester, polyolefin, rayon and the like which is substantially porous and permits body fluid to readily pass therethrough and into the underlying absorbent core. The topsheet material will preferably have no affinity for holding aqueous body fluids in the area of contact between the topsheet and the wearer's skin.

The absorbent core of the absorbent article embodiments of this invention can consist solely of one or more of the foam structures herein. For example, the absorbent core may comprise a single unitary piece off foam shaped as desired or needed to best fit the type of absorbent article in which it is to be used. Alternatively, the absorbent core may comprise a plurality of foam pieces or particles which may be adhesively bonded together or which may simply be constrained into an unbonded aggregate held together by an overwrapping of envelope tissue or by means of the topsheet and backing sheet of the absorbent article.

The absorbent core of the absorbent articles herein can also comprise other, e.g., conventional, elements or materials in addition to one or more foam absorbent structures of the present invention. For example, absorbent articles herein may utilize an absorbent core which comprises a combination, e.g., an airlaid mixture, of particles or pieces of the foam absorbent structures herein and conventional absorbent materials such as a) wood pulp or other cellulosic fibers, and/or, b) particles or fibers of polymeric gelling agents.

In one embodiment involving a combination of the foam absorbent material herein and other absorbent materials, the absorbent articles herein may employ a multi-layer absorbent core configuration wherein a core layer containing one or more foam structures of this invention may be used in combination with one or more additional separate core layers comprising conventional absorbent structures or materials. Such conventional absorbent structures or materials, for example, can include air-laid or wet-laid webs of wood pulp or other cellulosic fibers. Such conventional structures may also comprise conventional, e.g., large cell, absorbent foams or even sponges. The conventional absorbent structures used with the foam absorbent herein may also contain, for example up to 80% by weight, of particles or fibers of polymeric gelling agent of the type commonly used in absorbent articles that are to acquire and retain .aqueous body fluids. Polymeric gelling agents of this type and their use in absorbent articles are more fully described in Brandt/Goldman/Inglin, U.S. Reissue Pat. No. Re 32,649, Reissued Apr. 19, 1988, incorporated herein by reference.

One preferred type of absorbent article herein is one which utilizes a multi-layer absorbent core having an upper fluid acquisition/distribution layer, comprising a layer of modified cellulosic fibers, e.g., stiffened curled cellulosic fibers, and optionally up to about 10% by weight of this fluid acquisition/distribution layer of polymeric gelling agent. Such a multi-layer absorbent core also comprises a second, i.e., lower, fluid storage/redistribution layer comprising a foam structure of the present invention. (For purposes of this invention, an "upper" layer of a multi-layer absorbent core is a layer which is relatively closer to the body of the wearer, e.g., the layer closest to the article topsheet. The term "lower" layer conversely means a layer of a multi-layer absorbent core which is relatively further away from the body of the wearer, e.g., the layer closest to the article backsheet.) The modified cellulosic fibers used in the fluid acquisition/distribution layer of such a preferred absorbent article are preferably wood pulp fibers which have been stiffened and curled by means of chemical and/or thermal treatment. Such modified cellulosic fibers are of the same type as are employed in the absorbent articles described in Lash and Thompson; U.S. Pat. No. 4,935,622; Issued Jun. 19, 1990, incorporated herein by reference. Absorbent articles which utilize the absorbent foam structures of this invention in a fluid storage/redistribution layer underlying a fluid acquisition/distribution layer containing stiffened curled cellulosic fibers are described in greater detail in the U.S. Patent application of Gerald A. Young, Gary D. LaVon and Gregory W. Taylor having Ser. No. 743,950 (now U.S. Pat. No. 5,147,345, issued Sep. 15, 1992), concurrently filed herewith. This application is incorporated herein by reference.

As indicated hereinbefore, the fluid handling and mechanical characteristics of the specific foam absorbent structures herein render such structures especially suitable for use in absorbent articles in the form of disposable diapers. Disposable diapers comprising the foam absorbent structures of the present invention may be made by using conventional diaper making techniques, but by replacing or supplementing the wood pulp fiber web ("airfelt") or modified cellulosic core absorbents typically used in conventional diapers with one or more foam structures of the present invention. Foam structures of this invention may thus be used in diapers in single layer or, as noted hereinbefore, in various multiple layer core configurations. Articles in the form of disposable diapers are more fully described in Duncan and Baker, U.S. Pat. No. Re 26,151, Issued Jan. 31, 1967; Duncan, U.S. Pat. No. 3,592,194, Issued Jul. 13, 1971; Duncan and Gelleft, U.S. Pat. No. 3,489,148, Issued Jan. 13, 1970; Buell, U.S. Pat. No. 3,860,003, Issued Jan. 14, 1975; and Alemany and Berg; U.S. Pat. No. 4,834,735; Issued May 30, 1989; which patents are incorporated herein by reference.

Figure 2:
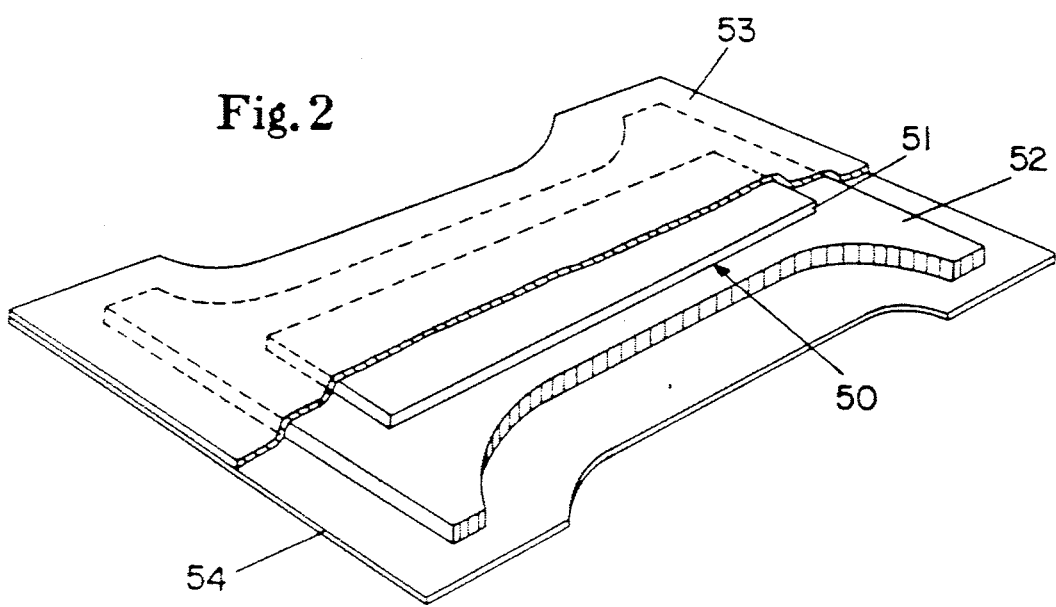
FIG. 2 of the drawings is a cutaway depiction of a disposable diaper which utilizes the absorbent foam material of the present invention as an- hourglass-shaped fluid storage/distribution component in an absorbent diaper core of dual-layer configuration.

A preferred disposable diaper embodiment of this invention is illustrated by FIG. 2 of the drawings. Such a diaper includes an absorbent core, 50, comprising an upper fluid acquisition layer, 51, and an underlying fluid storage/distribution layer, 52, comprising a foam absorbent structure of this invention. A topsheet, 53, is superposed and co-extensive with one face of the core, and a liquid impervious backsheet, 54, is superposed and coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another preferred type of absorbent article which can utilize the foam absorbent structures of the present invention comprises form-fitting products such as training pants. Such form-fitting articles will generally include a nonwoven, flexible substrate fashioned into a chassis in the form of briefs or shorts. A foam absorbent structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article may comprise cloth or paper or other kinds of nonwoven substrate or formed films and may be elasticized or otherwise stretch- able. Leg bands or waist bands of such training pants articles may be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in Roberts; U.S. Pat. No. 4,619,649; Issued Oct. 28, 1986, incorporated herein by reference.

Figure 3:
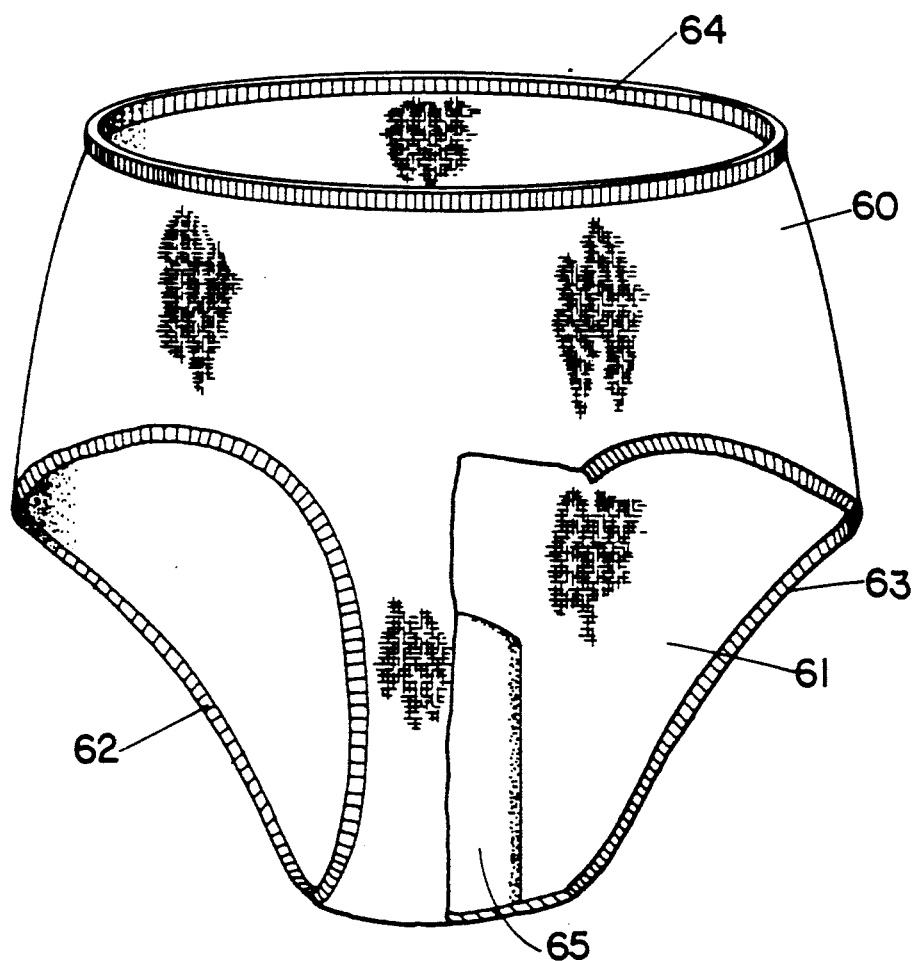
FIG. 3 of the drawings represents a cut-away view of a form-fitting article such as a disposable training pants product which employs an absorbent HIPE foam structure of this invention as an absorbent core.

A typical form-fitting article in the form of a disposable training pants product is shown in FIG. 3 of the drawing. Such a product comprises an outer layer, 60, affixed to a lining layer, 61, by adhesion along the peripheral zones thereof. For example, the inner lining, 61, may be affixed to the outer layer, 60, along the periphery of one leg band area, 62; along the periphery of the other leg band area, 63; and along the periphery of waistband area, 64. Affixed to the crotch area of the article is a generally rectangular absorbent core, 65, comprising a foam absorbent structure of the present invention.

TEST METHODS

In describing the present invention, a number of characteristics of the HIPE foam absorbent structures are set forth. Where reported, these characteristics can be determined using the following test fluids and test methods.

I) TEST FLUIDS AND FOAM SAMPLE PREPARATION

A) Test Fluid—Synthetic Urine

Several of the measurements described in the tests herein involve the use of a test fluid such as synthetic urine, ethanol, or isopropanol. The synthetic urine utilized in a number of the tests described hereinafter is made from a commercially available synthetic urine preparation manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_2*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of 65±5 dynes/cm.

B) Foam Sample Preparation

A number of the following tests involve the preparation and testing of foam samples of a particular specified size. Unless otherwise specified, foam samples of the requisite size should be cut from larger blocks of foam using a sharp reciprocating knife saw. Use of this or equivalent type of foam cutting device serves to substantially eliminate sample edge flaws which could have adverse impact on certain of the measurements made in carrying out the several test procedures hereinafter set forth.

Sample size specification will also generally include a dimension for sample caliper or thickness. Caliper or thickness measurements for purposes of the present invention should be made when the foam sample is under a confining pressure of 0.05 psi (350 Pa).

II) DETERMINATION OF STRUCTURAL CHARACTERISTICS

A) Available Pore Volume

A procedure for determining available pore volume involves the measurement of the amount of isopropanol (flash point 12° C.) which can be introduced into the structure of an absorbent foam sample. Equipment and materials used in making such a measurement are equilibrated at 22°±2° C. Measurements are also performed at this temperature.

Dry foam samples are cut into 1 in² (6.5 cm²)×0.3 inch (0.8 cm) thick cylinders or the equivalent. Such cylinderical samples can be prepared by using a sharp punch 1.13 inches (2.87 cm) in diameter on a 0.3 inch (0.8 cm) sheet of foam. The dry foam samples are each weighed to determine a dry weight (dw). Three of such samples are weighed to determine an average dry weight (DW).

The Measured Free Capacity (MFC) of these samples is then determined by the following steps:

1) The foam samples are immersed in the isopropanol in a crystallizing dish and allowed to saturate. At this point the sample may be squeezed a few times to expel air.

2) Each sample is removed without squeezing isopropanol out of it. Excess fluid is allowed to drip off of the sample in the flat position for about 30 seconds. Each sample is then weighed wet to determine a wet weight (ww).

3) Steps 1) and 2) are repeated two more times and an average wet weight (WW) is calculated.

Measured Free Capacity (MFC, g/g) is the weight of isopropanol in the saturated foam per unit mass of dry foam. MFC is calculated according to the formula $$MFC = \frac{[WW(g) - DW(g)]}{DW(g)}$$

Available pore volume is then calculated by dividing the MFC of the foam for isopropanol by the density of isopropanol which is 0.785 g/mL. This gives an available pore volume for the foam in mL/g.

B) Capillary Suction Specific Surface Area

Capillary Suction Specific surface area of the foam absorbents herein can be determined from the equilibrium weight uptake of a test liquid of known low surface tension. In this instance, absolute ethanol (flash point is 10° C.) is used.

To conduct the test, a tared foam sample strip of suitable dimensions (e.g., 25 cm long×2 cm wide×0.8 cm thick) is equilibrated at 22°±2° C., is positioned vertically and at one end is immersed 1-2 mm into a reservoir of the ethanol using a lab jack. The ethanol is allowed to wick up the foam strip to its equilibrium height which should be less than the sample length. The ethanol-containing strip is then weighed while still touching the reservoir to determine the weight of total ethanol uptake. During this procedure the sample should be shielded, for example with a capped glass cylinder, to prevent ethanol evaporation.

Specific surface area of the foam sample can be calculated from the following formula:

$$S_c = \frac{M_eGL_n}{M_n\gamma_e}$$

where $S_c$=capillary suction specific surface area in cm$^2$/gm; $M_e$=mass of liquid uptake of EtOH in gms; G=the gravitational constant which is 980 cm/sec$^2$; $L_n$=total length of sample in cm; $M_n$=mass of dry sample in gm; and $\gamma_e$=surface tension of EtOH which is 22.3 dynes/cm. Values obtained can then be divided by 10000 cm$^2$/m$^2$ to provide capillary suction specific surface area in m$^2$/g.

C) Foam Density

One procedure which can be used to determine foam density is that described in ASTM Method No. D3574-86, Test A, which is designed primarily for the testing of urethane foams but which can also be utilized for measuring density of the preferred HIPE-type absorbent foams of the present invention. In particular, density measurements made according to this ASTM procedure are carried out on foam samples which have been preconditioned in a certain manner as specified in that test.

Density is determined by measuring both the dry mass of a given foam sample and its volume at 22°±2° C. Volume determination on larger foam samples are calculated from measurements of the sample dimensions made under no confining pressure. Dimensions of smaller foam samples may be measured using a dial-type gauge using a pressure on the dial foot of 350 Pa (0.05 psi).

Density is calculated as mass per unit volume. For purposes of this invention, density is generally expressed in terms of g/cm$^3$.

III) DETERMINATION OF MECHANICAL CHARACTERISTICS

A) Resistance to Compression Deflection

Resistance to compression deflection can be quantified for purposes of this invention by measuring the amount of strain (% caliper reduction) produced in a foam sample, which has been saturated with synthetic urine, after stress in the form of a 0.74 psi (5.1 kPa) confining pressure has been applied to the sample.

Testing to make such measurements can be carried out on foam sample cylinders prepared as hereinbefore desired for the Available Pore Volume test. Such samples, the synthetic urine test fluid and equipment used to make measurements are all equilibrated in a constant temperature room heated to 99° F. (37° C.). Measurements are also performed in this room.

The foam samples are placed in a crystallizing dish and saturated to their free absorbent capacity with Jayco synthetic urine. A given saturated sample to be tested is then placed on a 25 mesh screen over a beaker, and a dial-type gauge suitable for making caliper measurements is positioned on the sample. Any gauge fitted with a foot having a surface area of at least 1 in$^2$ (6.5 cm$^2$) and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan). Also utilized are weights which can be used with the dial gauge to produce a foot pressure on the foam sample of up to 1.0 psi (6.9 kPa).

The saturated foam sample on the screen is subjected to a confining pressure of 0.74 psi (5.1 kPa) for 15 minutes. At the end of this time, the dial gauge is used to measure the change in sample caliper which occurs as a consequence of the application of the confining pressure. From the initial and final caliper measurements, a percent strain induced can be calculated for the sample.

B) Flexibility

Foam flexibility can be quantified by referencing a test procedure which is a modification of the ASTM D 3574-86, 3.3 test used to determine flexibility of cellular organic polymeric foam products. Such a modified test utilizes a foam sample which is 7×0.8×0.8 cm and which has been saturated to its free absorbent capacity with Jayco synthetic urine at 37° C. It is important that the cutting process used to make these samples does not introduce edge defects in the foam strip. The synthetic urine-saturated foam strip is bent around a 0.8 cm diameter cylindrical mandrel at a uniform rate of 1 lap in 5 seconds until the ends of the strip meet. The foam is considered flexible if it does not tear or break during this test, i.e., if it passes one bending cycle.

C) Recovery From Compression Deflection

To test recovery from compression deflection, foam samples similar to those prepared for the Available Pore Volume test hereinbefore described are used. Such samples are 0.8 cm thick cylinders having a cross-sectional circular area of 6.45 cm$^2$ (1 in$^2$). These foam samples may be tested in either the dry state or after they have been saturated to their free absorbent capacity with Jayco synthetic urine.

Using a dial-type gauge, a test sample, whether dry or wet, is compressed within 10 seconds to 50% of its original thickness and maintained in the compressed state for 1 minute. The pressure is then released, and the foam is allowed to recover thickness for 1 minute. The percent recovery is based on the original height of the uncompressed foam.

For testing of dry samples, ambient temperature, e.g., 22°±2° C., is used. For testing of wet samples, the foam sample is saturated to its free absorbent capacity with 37° C. Jayco synthetic urine in a 5 cm diameter dish. The dish acts as a reservoir to contain expressed fluid during the compression and also acts as a reservoir from which the sample can re-absorb fluid upon recovery from compression.

IV) DETERMINATION OF FLUID HANDLING CHARACTERISTICS

A) Absorbent Capacity

Both free absorbent capacity and absorbent capacity under pressure can be determined by a gravimetric analytical technique using synthetic urine as the fluid for which absorbent capacity of the foam is to be calculated.

1) principle of the Absorbent Capacity Testing

In this test, a foam sample is saturated with synthetic urine test liquid to measure the no-load or free absorbent capacity of the foam sample. Pressure is then applied in various increments to determine absorbent capacity under load. This absorbent capacity under pressure is measured after the foam sample has been held in a compressed state for a fixed amount of time.

2) Scope of Testing

This test measures the absorbent capacity of a foam sample under pressures of interest, namely from 0 to 1.0 pound per square inch (psi) (0 to 6.9 kPa), and at the temperature of interest, i.e., 99° F. (37° C.).

3) Equipment

Screen, 25 mesh, 8 cm in diameter; crystallizing dish, 15 cm diameter×7.5 cm high; beaker, 50 mL; analytical balance; dial-type gauge, fitted with a foot at least 1 in$^2$ (6.5 cm$^2$) and capable of measuring to 0.001 inch (0.025 mm), e.g., Ames model 482 (Ames Co., Waltham, Mass.) or Ono-Sokki model EG-225, Ono-Sokki Co., Ltd., Japan); weights for the dial-type gauge capable of producing pressures of 0.2, 0.74, and 1.0 psi (1.4, 5.1, and 6.9 kPa).

4) Materials

JAYCO synthetic urine; foam samples.

5) Procedure i) The equipment and materials hereinbefore described are equilibrated in a constant temperature room heated to 99° F. (37° C.). Measurements are also performed in this room.

ii) Foam samples similar to those prepared as in the Available Pore Volume test are cut into 1 in$^2$ (6.5 cm$^2$)×0.3 in (0.8 cm) thick cylinders. These samples are weighed to provide an average dry weight (DW).

iii) Free Absorbent Capacity (FAC) of each foam sample is determined as follows:
  a) The foam sample is immersed into the synthetic urine in the crystallizing dish and allowed to saturate. The sample may be squeezed a few times to expel air.
  b) The foam is removed without squeezing fluid out of it. Excess fluid is allowed to drip off of the sample in the flat position for about 30 seconds, and then the wet sample is weighed.
  c) Steps a) and b) are repeated two more times and an average wet weight (WW) is calculated.
  d) The Free Absorbent Capacity (FAC, g/g is calculated as $$FAC = \text{weight synthetic urine in saturated foam/dry weight foam}$$
$$= [WW(g) - DW(g)]/DW(g)$$

iv) Absorbent Capacity Under Pressure (Pressure Desorption) for each foam sample is determined as follows:
  a) The 50 mL beaker, with the screen on top of it, is positioned under the center of the foot of the dial-type gauge, with the foot resting on the screen.
  b) The saturated sample is placed on top of the screen, making sure the sample is over the center of the beaker, and the dial-type gauge is positioned to apply confining pressure on the foam sample.
  c) Weights are placed on the gauge to apply 0.2 psi (1.4 kPa) of pressure on the sample.
  d) After 15 minutes, the foam sample is weighed (WW,0.2).
  e) The same sample is resaturated, and then steps a)-d) are repeated except the 0.74 and 1.0 psi are used to determine WW,0.74 and WW,1.0.
  f) Using new samples, steps a)-e) are repeated two more times to determine average wet weights after the samples are held under the different pressures.
  g) Absorbent capacities under pressure (X-load, g/g are calculated as shown. (X-load under a given pressure is the weight synthetic urine in wet foam/dry weight foam.)

Capacity under 0.2 psi $$X,0.2 \text{ (g/g)} = [WW,0.2 \text{ (g)} - DW \text{ (g)}]/DW \text{ (g)}$$

Capacity under 0.74 psi $$X,0.74 \text{ (g/g)} = [WW,0.74 \text{ (g)} - DW \text{ (g)}]/DW \text{ (g)}$$

Capacity under 1.0 psi $$X,1.0 \text{ (g/g)} = [WW,1.0 \text{ (g)} - DW \text{ (g)}]/DW \text{ (g)}$$

Absorbent capacity values in mL of synthetic urine per gram of dry foam can be obtained by dividing the FAC and the X-load values by the specific gravity of the Jayco synthetic urine which is approximately 1 g/mL.

B) Vertical Wicking Rate and Vertical Wicking Absorbent Capacity

Vertical wicking rate and vertical wicking absorbent capacity are measures of the ability of a dry foam to wick fluid vertically from a reservoir. The time required for the fluid front to wick through a 5 cm vertical length of a strip of foam is measured to give a vertical wicking rate. After fluid wicks to its equilibrium height, the amount of fluid held by the foam strip at a particular vertical wicking height (e.g., 4.5 inches or 11.4 cm) is determined to give a vertical wicking absorbent capacity.

Jayco synthetic urine colored with blue food coloring is used in the following methods to determine vertical wicking rate and vertical wicking absorbent capacity. In this test procedure, the materials are equilibrated at 37° C. and the test is performed at the same temperature.

1) Sample Preparation
  i) A strip of foam approximately 25 cm×2 cm×0.8 cm is prepared as in the Capillary Suction Specific Surface Area test.
  ii) A fluid reservoir is placed on top of a lab jack and the foam sample is clamped at one end so that it is suspended vertically over the fluid reservoir.
  iii) A ruler is clamped next to the foam sample so that the bottom (0 cm) of the ruler is about 1-2 mm above the bottom of the foam sample.
  iv) The fluid reservoir is filled about ¾ full with the dyed synthetic urine solution.

2) Vertical Wicking Rate
  i) The reservoir is raised up to the bottom of the foam sample with the lab jack. A timer is started as soon as the fluid touches the bottom of the foam sample.
  ii) The reservoir is immediately raised until the liquid just touches the bottom of the ruler.
  iii) The time it takes the fluid front to reach 5 cm is recorded.
  iv) The foam is allowed to wick until it reaches equilibrium (e.g., about 18 hours). The lab jack may need to be adjusted to keep 1-2 mm of the sample immersed, and the sample should be shielded to prevent evaporation.

3) Absorbent Capacity (mL/g) per Vertical Length of Foam
  i) The foam sample is removed and quickly placed on a non-absorbent surface.
  ii) The sample is immediately cut into separate 1 inch (2.54 cm) pieces using a tool sharp enough not to compress the foam sample, and each such piece is weighed.

iii) Most of the fluid is squeezed out of each piece, and each piece is placed on an absorbent towel.

iv) Each piece is allowed to dry completely.

v) Each dry piece is then weighed and an absorbent capacity for each piece is calculated based on the difference between the wet and dry weights. For purposes of the present invention, the absorbent capacity of the one-inch segment which represents 4.5 inches (11.4 cm) of wicking height is the parameter most desirably determined.

C) Adhesion Tension

The adhesion tension exhibited by hydrophilized foam samples which imbibe test fluids via capillary suction is the product of the surface tension, $\gamma$, of the test fluid times the cosine of the contact angle, $\theta$, exhibited by the test fluid in contact with the interior surfaces of the foam sample. Adhesion tension can be determined experimentally by measuring the equilibrium weight uptake by capillary suction exhibited by two test samples of the same foam using two different test liquids. In the first step of such a procedure, specific surface area of the foam sample is determined using ethanol as the test fluid as described hereinbefore in the Specific Surface Area discussion of this TEST METHODS section.

The capillary suction uptake procedure is then repeated in identical manner to the ethanol procedure except that JAYCO synthetic urine is used as the test fluid and the test is carried out at 37° C. Contact angle of the synthetic urine can then be calculated as follows from the known specific surface area and the synthetic urine uptake data:

$$\cos\Theta_U = \frac{M_U G L_N}{M_N \gamma_U S_c}$$

where $\theta_U$ = contact angle of Jayco synthetic urine in degrees; $M_U$ = mass of liquid uptake of Jayco synthetic urine in gms; G = gravitational constant which is 980 cm/sec$^2$; $M_N$ = mass of dry foam sample in gm; $\gamma_U$ = surface tension of JAYCO urine which is −65 dynes/cm; $S_c$ = specific surface area of the foam sample in cm$^2$/gm as determined by the ethanol uptake procedure; and $L_n$ = length of the foam sample in cm.

When a surfactant is present (on the foam sample surfaces and/or in the advancing test liquid), characterization of the advancing liquid front is defined by applying the adhesion tension (AT) equation:

$$AT = \frac{M_T G L_N}{M_N S_c}$$

wherein $M_T$ is the mass of the test liquid taken up by the foam sample, and G, $L_N$, $M_N$, and $S_c$ are as hereinbefore defined. [See Hodgson and Berg, *J. Coll. Int. Sci.*, 121(1), 1988, pp 22-31]

In determining adhesion tension for any given test liquid, no assumption is made of the numerical value of the surface tension at any point in time so that possible changes in surfactant concentration on the sample surfaces and/or in the advancing liquid during wicking are immaterial. The experimental value of adhesion tension ($\gamma\cos\theta$) is especially useful when viewed as a percentage of the maximum adhesion tension which is the surface tension of the test liquid (e.g., the maximum adhesion tension using JAYCO synthetic urine would be [65±5] [cos 0°] = 65±5 dynes/cm).

EXAMPLES

Preparation of HIPE absorbent foam materials, the characteristics of such foam materials and utilization of these foam absorbents in a disposable diaper are all illustrated by the following examples.

EXAMPLE I

Preparation of a preferred HIPE foam absorbent on a semi-pilot plant scale is illustrated by this example.

Emulsion Preparation

Calcium chloride (320 g.) and potassium persulfate (48 g.) are dissolved in 32 liters of distilled water. This provides the water phase used to form the HIPE emulsion.

To a monomer combination comprising styrene (420 g.), divinylbenzene (660 g.) and 2-ethylhexylacrylate (1920 g.) are added sorbitan monooleate (450 g. as SPAN® 80) and sorbitan trioleate (150 g. as SPAN® 85). After mixing, this comprises the oil phase used to form the HIPE emulsion.

At liquid temperatures in the range of 55° C. to 65° C., separate streams of the oil phase and water phase are fed to a dynamic mixing chamber. Thorough mixing of the combined streams in the dynamic mixing chamber is achieved by means of a pin impeller. At this scale of operation, an appropriate pin impeller comprises a cylindrical shaft of about 18 cm in length with a diameter of about 1.9 cm. The shaft holds two rows of 17 and two rows of 16 cylindrical pins each having a diameter of 0.5 cm extending radially outward from the central axis of the shaft to a length of 1.6 cm. The four rows are positioned at 90° angles around the circumference of the impeller shaft. The rows that are perpendicular to each other are offset along the length of the shaft such that no pins which are perpendicular to each other are in the same radial plane extending from the axis of the shaft. The pin impeller is mounted in a cylindrical sleeve which forms the dynamic mixing chamber, and the pins in the impeller have a clearance of 0.8 mm from the walls of the cylindrical sleeve. The impeller is operated at a speed of 900 revolutions per minute.

A static mixer (8 inches long by ¼ inch outside diameter by 0.190 inch inside diameter) is mounted further downstream from the dynamic mixing chamber to help provide some back pressure. This helps keep the dynamic mixing chamber comprising the cylindrical sleeve with its pin impeller full. This also helps to ensure appropriate and complete mixing of the oil and water phases.

An emulsion having the requisite ratio of water to oil phases is approached gradually. At first, flow rates are adjusted so that 3 parts by weight of the water phase and 1 part by weight of the oil phase enter the dynamic mixing chamber with the pin impeller. The water to oil phase ratio is increased, over a period of a few minutes, until a ratio of 12-13 parts water phase to 1 part oil phase is passing into the dynamic mixing chamber, at a rate of 15 mL/sec. Gradually, the oil flow rate is decreased so that the water phase/oil phase weight ratio is near 25:1. At this stage, the viscosity of the emulsion flowing out of the static mixer drops. (Visually, the whitish mixture becomes more translucent at this point.)

The flow rate of the oil phase is thereafter further decreased to the point where the water phase/oil phase weight ratio is 30–33:1. Visually, the emulsion at this stage flows from the static mixer orifice with the consistency of a whipping cream and "sets" to a consistency reminiscent of a creamy yogurt.

Polymerization of the Emulsion

At this point, the emulsion emerging from the static mixer is ready for curing. The emulsion is fed to a generally rectangular mold which is made of polyethylene and which has the dimensions, 38 cm length; 25 cm width and 22 cm depth. Emulsion is emptied into such molds until each mold contains approximately 20,000 mL of the emulsion to be cured.

Curing is effected by placing the emulsion-containing molds in a curing oven at a temperature of 60° C. for a period of about 16 hours. After curing, the resulting solid polymerized foam material contains up to 98% water and is soft and sopping wet to the touch.

Foam Washing and Hydrophilization

The wet cured foam material is removed from the curing mold and subjected to further processing. The residual water phase in the foam is expressed by applying sufficient pressure to the foam material, or to thin slices of the foam material, to squeeze out at least 90% of the retained original residual water phase material. Notably, when the foam prepared according to the foregoing procedure is squeezed, the edges of the foam do not extrude outwardly, and the cells of the foam do not burst. Rather, the foam appears to collapse under pressure in the Z-direction and then spring back to its original shape, either as water is imbibed or when heat is applied as described more fully hereinafter.

The foam sample is then washed for 20 seconds in 60° C. water containing a detergent as a hydrophilizing agent. In this example, the detergent is JOY brand dishwashing liquid which is dissolved in water to the extent of 5 g/liter. The active hydrophilizing agents in the JOY product comprise a mixture of coconut alkyl sulfate and ethoxylated coconut alkyl sulfate anionic surfactants as described more fully in Pancheri; U.S. Pat. No. 4,316,824; Issued Feb. 23, 1982 (incorporated herein by reference). During this treatment, the foam springs back to its original shape.

The JOY solution used in the first washing is again expressed using pressure, and the foam is then treated with a second washing with the JOY solution at 60° C. This second rinse is intended to leave a residue of detergent in the foam, thereby rendering the internal foam surfaces relatively hydrophilic.

Foam Dewatering

The twice hydrophilized foam is then again pressed to express excess detergent solution from within its porous structure. The foam samples are then dried by subjecting them to oven drying for 12 hours at 60° C. After drying the foam samples are further cut or sliced if necessary and are provided for further testing or for incorporation into diaper products of the type described hereinafter in Example IV.

EXAMPLE II

Another HIPE foam material is prepared in the the same general manner as set forth hereinbefore in Example I. In this example, the emulsion preparation and polymerization procedures are carried out as in Example I but with the following differences in materials, concentrations and conditions:

1) An emulsifier mixture of 480 g of SPAN ® 80 and 120 g of SPAN ® 85 is used in the oil phase.
2) A 14 inch long×⅜ inch O.D. (35.6 cm×0.95 cm) static mixer is used downstream from the mixing chamber.
3) The pin impeller is operated at a speed of 850 revolutions per minute.
4) The final water to oil phase weight ratio is 31:1.
5) A curing temperature of 66° C. is used.

In this example, the polymerized HIPE foam is hydrophilized by treatment with an aqueous solution of calcium chloride as the hydrophilizing agent. This hydrophilizing agent solution contains 1% by weight of calcium chloride and is applied to the foam samples twice in the same manner as in Example I. After drying, the foam samples of this example are then further cut or sliced as needed for additional testing and for incorporation into diaper products of the type described hereinafter in Example IV.

EXAMPLE III

In this example, HIPE foam materials prepared according to the general procedures of Examples I and II are tested for their structural, mechanical and fluid handling properties. Testing to determine these properties is carried out using the procedure described in the hereinbefore referred U.S. Pat. No. 4,788,225 or the several procedures set forth hereinbefore in the TEST METHODS section. The results of such testing are summarized as follows in Table I.

TABLE I

| FEATURE | EXAMPLE I FOAM | EXAMPLE II FOAM | Units |
| --- | --- | --- | --- |
| Structural Features | | | |
| Pore Volume | 36.8 | 31.8 | mL/g |
| Capillary Suction Specific Surface Area | 1.35 | 1.25 | m²/g |
| Density | 0.029 | 0.032 | g/cm³ |
| Average Cell Size | 40 | 37 | μ |
| Mechanical Features | | | |
| Strain Under 5.1 kPa Confining Pressure | 52% | 31% | % |
| Flexibility | >1 | >1 | bending cycles |
| % Recovery From 50% Compression | 95% | 94% | % |
| Fluid Handling Properties | | | |
| Absorbent capacity under a pressure of: | | | |
| 0.0 kPa (0.0 psi) | 35.9 | 31.5 | mL/g |
| 1.4 kPa (0.2 psi) | 34.0 | 29.1 | mL/g |
| 5.1 kPa (0.74 psi) | 23.4 | 25.1 | mL/g |
| 6.9 kPa (1.0 psi) | 13.0 | 14.8 | mL/g |
| % of 0.0 kPa capacity at 5.1 kPa | 65.2 | 79.7 | % |
| Vertical wicking time to 5 cm | 105 | 120 | sec |
| Absorbent capacity at a height up to: | | | |
| 1.3 cm (0.5 in) | 30.9 | 26.7 | mL/g |
| 3.8 cm (1.5 in) | 30.7 | 26.4 | mL/g |
| 6.4 cm (2.5 in) | 28.0 | 25.3 | mL/g |
| 8.9 cm (3.5 in) | 26.6 | 24.8 | mL/g |
| 11.4 cm (4.5 in) | 18.7 | 24.0 | mL/g |
| 14.0 cm (5.5 in) | 0.6 | 23.3 | mL/g |
| 16.5 cm (6.5 in) | 0 | 21.8 | mL/g |
| 19.1 cm (7.5 in) | 0 | 14.1 | mL/g |
| Adhesion Tension in 65 ± 5 dynes/cm Synthetic Urine | 30.7 | 37.8 | dynes/cm |

EXAMPLE IV

Figure 4:
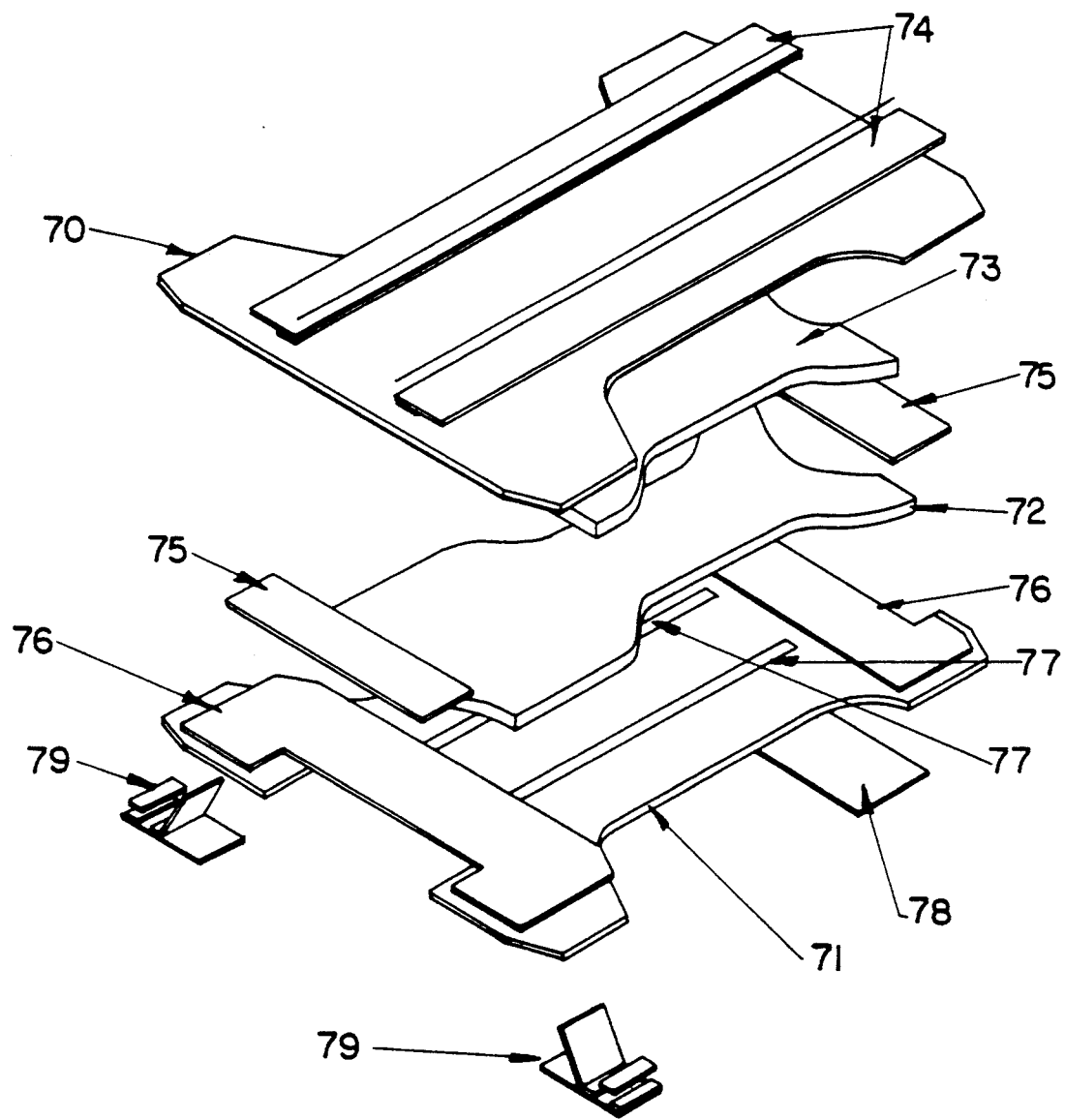
FIG. 4 of the drawings represents a blown-apart view of the components of a diaper structure also of dual layer core configuration having an hourglass-shaped fluid acquisition layer overlying an absorbent foam fluid storage/distribution layer with a modified hourglass shape.

A disposable diaper is prepared using the configuration and components shown in expanded and blown-apart depiction in FIG. 4. Such a diaper comprises a thermally bonded polypropylene topsheet, 70, a fluid-impervious polyethylene backing sheet, 71, and a dual layer absorbent core positioned between the topsheet and the backing sheet. The dual layer absorbent core comprises a modified hourglass-shaped, fluid storage/-redistribution layer, 72, comprising HIPE foam of the Example II type positioned below a modified-hourglass shaped fluid acquisition layer, 73. The topsheet contains two substantially parallel barrier leg cuff strips, 74, with elastic. Affixed to the diaper backsheet are two rectangular elasticized waistband members, 75. Also affixed to each end of the polyethylene backsheet are two waistshield elements, 76, constructed of polyethylene. Also affixed to the backsheet are two parallel leg elastic strips, 77. A sheet of polyethylene, 78, is affixed to the outside of the backsheet as a dedicated fastening surface for two pieces, 79, of Y type which can be used to fasten the diaper around the wearer.

The acquisition layer of the diaper core comprises a 92%/8% wetlaid mixture of stiffened, twisted, curled cellulosic fibers and conventional non-stiffened cellulosic fibers. The stiffened, twisted, curled cellulosic fibers are made from southern softwood kraft pulp (Foley fluff) which has been crosslinked with glutaraldehyde to the extent of about 2.5 mole percent on a dry fiber cellulose anhydroglucose basis. The fibers are crosslinked according to the "dry crosslinking process" as described in Dean, Moore, Owens and Schoggen; U.S. Pat. No. 4,822,453; Issued Apr. 18, 1989.

These stiffened fibers are similar to the fibers having the characteristics described as follows in Table II.

TABLE II

Stiffened, Twisted, Curled Cellulose (STCC) Fibers

Type = Southern softwood kraft pulp crosslinked with glutaraldehyde to the extent of 1.41 mole percent on a dry fiber cellulose anhydroglucose basis Twist Count Dry = 6.8 nodes/mm
Twist Count Wet = 5.1 nodes/mm
Isopropol Alcohol Retention Value = 24%
Water Retention Value = 37%
Curl Factor = 0.63

The conventional non-stiffened cellulose fibers used in combination with the STCC fibers are also made from Foley fluff. These non-stiffened cellulose fibers are refined to about 200 CSF (Canadian Standard Freeness).

The acquisition layer has an average dry density of about 0.07 g/cm$^3$, an average density upon saturation with synthetic urine, dry weight basis, of about 0.08 g/cm$^3$, and an average basis weight of about 0.03 g/cm$^2$. About 9.2 grams of the fluid acquisition layer are used in the diaper core. The surface area of the acquisition layer is about 46.8 in$^2$ (302 cm$^2$). It has a caliper of about 0.44 cm.

The fluid storage/redistribution layer of the diaper core comprises a modified hourglass-shaped piece of HIPE foam of the type described hereinbefore in Examples II and III. About 12 grams of HIPE foam are used to form this storage/distribution layer which has a surface area of about 65.9 in$^2$ (425 cm$^2$) and a caliper of about 0.325 in (0.826 cm).

A diaper having this particular core configuration exhibits especially desirable and efficient utilization of the core for holding discharged urine and accordingly provides exceptionally low incidence of leakage when worn by an infant in the normal manner.

EXAMPLE V

Diapers substantially similar to that described in Example IV are tested for efficacy in a panel test wherein 75 male infants use both the Example IV type diapers and control diaper products of conventional configuration in an overnight wearing situation. In such a test each panelist is given for use on consecutive nights 7 medium size diapers, 4 of the Example IV type and 3 of a type corresponding to the commercially marketed LUVS Deluxe for Boys product. The LUVS product is of the Customized Absorbency Zone for Boys configuration and contains 39.1 grams of absorbent material.

Caregivers are asked to use one diaper per night and to record and report the incidence of overnight leakage of each diaper used. Leakage results from all the panelists are then collected and analyzed. As a result of this analysis, it can be determined that, in such a panel test, 13.1% of the Example IV type diapers leak whereas 14.0% of the LUVS diapers leak.

This panel testing indicates that diapers utilizing the absorbent foam materials of the present invention as a fluid storage element can provide leakage performance which is comparable to that of commercially marketed control diaper products even though the diapers of the present invention contain significantly less absorbent material than do the control diaper products.

EXAMPLE VI

This example illustrates the preparation of another type of HIPE foam material falling within the scope of the present invention.

Emulsion Preparation

Calcium chloride (36.32 kg) and potassium persulfate (568 g) are dissolved in 378 liters of water. This provides the water phase stream to be used in a continuous process for forming a HIPE emulsion.

To a monomer combination comprising styrene (1600 g), divinylbenzene 55% technical grade (1600 g), and 2-ethylhexylacrylate (4800 g) is added sorbitan monolaurate (960 g as SPAN ® 20). After mixing, this combination of materials is allowed to settle overnight. The supernatant is withdrawn and used as the oil phase in a continuous process for forming a HIPE emulsion. (About 75 g of a sticky residue is discarded.)

At an aqueous phase temperature of 48°–50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft, as described in Example I, holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are 15"×23"×9" (38.1 cm×58.4 cm×22.9 cm). These boxes are pretreated with a film of a solution comprising a 20% solution of SPAN® 20 in an equal weight solvent mixture of xylene and isopropanol. The solvent mixture is allowed to evaporate to leave only the SPAN® 20. Forty-seven liters of emulsion are collected in each box.

The emulsion-containing boxes are kept in a room maintained at 65° C. for 18 hours to bring about polymerization of the emulsion in the boxes to thereby form polymeric foam material.

Foam Washing, Hydrophilization and Dewatering

After curing is complete, the wet cured foam material is removed from the curing boxes. The foam at this point contains about 30–40 times the weight of polymerized material (30–40×) of the residual water phase containing dissolved emulsifiers, electrolyte and initiator. The foam material is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6×) the weight of the polymerized material. At this point, the sheets are then resaturated with a 1% CaCl$_2$ solution at 60° C., are squeezed in a nip to a water phase content of about 10×, resaturated with the 1% CaCl$_2$ solution at 60° C., and then squeezed again in a nip to a water phase content of about 10×.

The foam sheets, which now contain about 10× of what is essentially a 1% CaCl$_2$ solution are passed through a final nip equipped with a vacuum slot. The last nip reduces the CaCl$_2$ solution content to about 5 times (5×) the weight of polymer. The foam remains compressed after the final nip at a caliper of about 0.080 in. (0.2 cm). The foam is then dried in an air circulating oven set at about 60° C. for about three hours. Such drying reduces the moisture content to about 5–7% by weight of polymerized material. At this point, the foam sheets have a caliper of about 0.075 in. (0.19 cm) and are very drapeable. The foam also contains about 11% by weight of residual sorbitan monolaurate emulsifier and about 5% by weight (anhydrous basis) of residual hydrated calcium chloride as hydrophilizing agents. In the collapsed state, the density of the foam is about 0.17 g/cm$^3$. When expanded to its free absorbent capacity (26.5 mL/g) in JAYCO synthetic urine, the expanded foam has a capillary suction specific surface area of about 2.24 m$^2$/g, a pore volume of about 29.5 cc/g and an average cell size of about 15 microns.

The foam sheets prepared as in Example VI represent a preferred "thin-until-wet" embodiment of the present invention inasmuch as these foam sheets are in the form of collapsed foam material which will expand upon contact with aqueous body fluids. Once expanded, the foam materials are useful for absorbing the body fluids that have caused the foam to expand. Such preferred collapsed foams are those which are formed from a non-hydrolyzed polymeric material, which have a capillary suction specific surface area of from about 0.5 to 5.0 m$^2$/g, and which contain from about 0.5% to 20% by weight of the foam material of residual water-insoluble emulsifier and from about 0.1% to 7% by weight (anhydrous basis) of the foam material of a toxicologically acceptable, hygroscopic, hydrated salt, which is preferably calcium chloride or magnesium chloride, as a hydrophilizing agent.

In its collapsed state, such foam material will have a residual water content of from about 4% to 15% by weight of polymerized material when it is stored at ambient conditions of 72° F. (22° C.) and 50% relative humidity. This water content includes both water of hydration associated with the hygroscopic, hydrated salt as well as free water absorbed within the foam. Such collapsed foam material will also have a dry basis density ranging from about 0.08 to 0.3 g/cm$^3$.

In its expanded state, such preferred thin-until-wet foam materials will have a pore volume from about 12 to 100 mL/g and will exhibit a resistance to compression deflection such that a confining pressure of 5.1 kPa produces after 15 minutes of strain from about 5% to 95% compression of the structure when it is saturated at 37° C. to its free absorbent capacity with synthetic urine having a surface tension of 65±5 dynes/cm. The average cell size of these preferred thin-until-wet foam materials in the expanded state will range from about 5 to 30 microns. The dry basis density of the expanded foam material upon saturation to its free absorbent capacity in this synthetic urine will range from about 9% to 28% of its dry basis density in the collapsed state.

EXAMPLE VII

A diaper substantially similar in configuration to that described in Example IV is prepared using as the fluid storage/redistribution layer a sheet of thin-until-wet collapsed absorbent foam of the type described in Example VI. In such a diaper, the fluid acquisition/distribution layer, comprising the stiffened, twisted, curled cellulosic fibers, is used in an amount of about 13 grams.

The thin-until-wet fluid storage/redistribution layer is also used in an amount of about 13 grams.

A diaper having this particular configuration exhibits especially desirable and efficient utilization of the absorbent core for holding discharged urine and accordingly provides exceptionally low incidence of leakage when worn by an infant in the normal manner.

What is claimed is:

1. A polymeric foam material especially suitable for absorbing and retaining aqueous body fluids, said foam material, when washed and dried, comprising a hydrophilic, flexible structure of interconnected open cells having sufficient residual hydrophilizing agent comprising a non-irritating surfactant to render the surface of the structure hydrophilic, which structure has, when in contact with aqueous body fluids:
   A) a pore volume of from about 12 to 100 mL/g;
   B) a specific surface area of from about 0.5 to about 5.0 m$^2$/g as determined by capillary suction; and
   C) a resistance to compression deflection such that a confining pressure of 5.1 kPa produces after 15 minutes a strain of from about 5% to 95% compression of the structure when it is saturated at 37° C. to its free absorbent capacity with synthetic urine having a surface tension of 65±5 dynes/cm.

2. A foam material according to claim 1 wherein
   A) the structure of the foam material comprises a polymerized water-in-oil emulsion, which emulsion prior to polymerization comprises
      a) an oil phase comprising
         i) from about 3% to 41% by weight of a substantially water-insoluble, monofunctional glassy monomer component;
         ii) from about 27% to 73% by weight of a substantially water-insoluble, monofunctional rubbery comonomer component;
         iii) from about 8% to 30% by weight of a substantially water-insoluble, polyfunctional cross-linking agent component, and
         iv) from about 2% to 33% by weight of an emulsifier component which is soluble in the oil phase and which is suitable for forming a stable water-in-oil emulsion; and
      b) a water phase comprising an aqueous solution containing from about 0.2% to 40% by weight of water-soluble electrolyte; the weight ratio of said water phase to said oil phase comprising said emulsion ranging from 12:1 to 100:1; and
   B) the structure of the foam material is hydrophilic to the extent that the structure exhibits an adhesion tension of from about 15 to 65 dynes/cm when absorbing synthetic urine having a surface tension of 65±5 dynes/cm.

3. A polymeric foam material according to claim 2 wherein in the water-in-oil emulsion precursor of the polymeric foam structure;
   a) the substantially water-insoluble, monofunctional glassy monomer component of the oil phase comprises one or more styrene-based monomer types;
   b) the substantially water-insoluble, monofunctional rubbery comonomer component of the oil phase comprises comonomer types selected from butylacrylate, 2-ethylhexylacrylate, butadiene, isoprene and combinations of these comonomer types;
   c) the molar ratio of monofunctional glassy monomer component to monofunctional rubbery comonomer component in the oil phase ranges from about 1:25 to 1.5:1;
   d) the substantially water-insoluble cross-linking agent component of the oil phase comprises a difunctional monomer type selected from divinylbenzene, divinyltoluene, diallyphthalate, one or more diacrylic acid esters of a polyol or combinations of such difunctional monomer types;
   e) the emulsifier component of the oil phase comprises an emulsifier selected from sorbitan fatty acid esters, polyglycerol fatty acid esters, polyoxyethylene fatty acids and esters and combinations of such emulsifiers;
   f) the water-soluble electrolyte in the water phase comprises one or more water-soluble salts of an alkali metal or alkaline earth metal;
   g) the water phase additionally comprises from about 0.02% to 0.4% by weight of a water-soluble, free radical polymerization initiator; and
   h) the weight ratio of water phase to oil phase comprising the emulsion ranges from about 20:1 to 70:1.

4. A polymeric foam material according to claim 3 wherein the foam structure has, when in contact with aqueous body fluids:
   (a) a density of from about 0.01 to 0.08 g/cm$^3$ on a dry weight basis;
   (b) an average cell size ranging from about 5 to 100 microns; and
   (c) a recovery from compression defection such that said structure recovers in one minute at least 85%, when dry at 20° C., or at least 75%, when saturated to its free absorbent capacity with 37° C. synthetic urine having a surface tension of 65±5 dynes/cm, of its original thickness after being compressed for one minute.

5. A polymeric foam material according to claim 3 which is flexible to the extent that it exhibits a bending value of at least one cycle when saturated with 37° C. synthetic urine.

6. A polymeric foam material according to claim 5 which is substantially free of polar functional groups on its polymeric structure but which is hydrophilic to the extent that it exhibits an adhesion tension of from about 20 to 65 dynes/cm when absorbing synthetic urine having a surface tension of 65±5 dynes/cm.

7. A polymeric foam material according to claim 6 which contains from about 0.1% to 10% by weight of a residual hydrophilizing agent selected from non-irritating surfactants and water-hydratable inorganic salts.

8. A polymeric foam material according to claim 7 which contains from about 0.1% to 7% by weight of a calcium chloride hydrophilizing agent.

9. A polymeric foam material according to claim 5 which has a free absorbent capacity at 37° C. of at least about 12 mL of synthetic urine having a surface tension of 65±5 dynes/cm per gram of dry foam material and which has an absorbent capacity for said synthetic urine under a confining pressure of 5.1 kPa maintained for 15 minutes at 37° C. which is at least about 5% of its free absorbent capacity.

10. A polymeric foam material according to claim 9 which exhibits a vertical wicking rate at 37° C. such that synthetic urine having a surface tension of 65±5 dynes/cm wicks along a 5 cm vertical length of foam in 30 minutes or less and which exhibits a vertical wicking absorbent capacity of at least 10 mL of said synthetic urine per gram of foam at a vertical wicking height of 11.4 cm.

11. A polymeric foam material especially suitable for absorbing and retaining aqueous body fluids, said foam material, when washed and dried, comprising a hydrophilic, flexible structure of interconnected open cells, which structure comprises a polymerized water-in-oil emulsion, which emulsion prior to polymerization comprises (A) an oil phase comprising
        (i) from about 7% to 40% by weight of styrene monomer;
        (ii) from about 27% to 66% by weight to a comonomer selected from butylacrylate, 2-ethylhexylacrylate, isoprene, and combinations of these comonomers;
        (iii) from about 10% to 25% by weight of a divinylbenzene cross-linking agent, and
        (iv) from about 4% to 25% by weight of an emulsifier component which comprises sorbitan monooleate and sorbitan trioleate in a monooleate to trioleate weight ratio of from about 2:1 to 5:1; and
    (B) a water phase comprising an aqueous solution containing from about 0.5% to 20% by weight of calcium chloride and from about 0.1% to 0.2% by weight of a water-soluble, free radical polymerization initiator;

wherein the weight ratio of said water phase to said oil phase comprising said emulsion ranges from 20:1 to 70:1; said structure containing from about 0.5 to 5% by weight of residual non-irritating surfactant and from about 0.1% to 7% by weight of residual calcium chloride as a hydrophilizing agent; said structure further having when in contact with said aqueous body fluids:

a) a pore volume of from about 20 to 70 mL/g;
    b) a specific surface area of from about 0.75 to 4.5 $m^2/g$ as determined by capillary suction; and
    c) a resistance to compression deflection such that a confining pressure of 5.1 kPa produces after 15 minutes a strain of from about 5% to 75% compression of the structure when it is saturated at 37° C. to its free absorbent capacity with synthetic urine having a surface tension of 65±5 dynes/cm.

* * * * *